US008980265B2

(12) United States Patent
Pfizenmaier et al.

(10) Patent No.: US 8,980,265 B2
(45) Date of Patent: Mar. 17, 2015

(54) SITE-SPECIFIC ANTIBODY-MEDIATED ACTIVATION OF PROAPOPTOTIC CYTOKINES: AMAIZEE (ANTIBODY-MEDIATED APOPTOSIS INDUCING CYTOKINES)

(75) Inventors: Klaus Pfizenmaier, Tiefenbronn (DE); Harald Wajant, Leinfelden-Echterdingen (DE); Dieter Moosmayer, Berlin (DE); Thomas Wuest, Dietikon (CH)

(73) Assignee: BioNTech AG (DE)

( * ) Notice: Subject to any disclaimer, the term of this patent is extended or adjusted under 35 U.S.C. 154(b) by 665 days.

(21) Appl. No.: 10/389,223

(22) Filed: Mar. 14, 2003

(65) Prior Publication Data

US 2004/0033511 A1 Feb. 19, 2004

Related U.S. Application Data

(63) Continuation of application No. PCT/EP01/10364, filed on Sep. 7, 2001.

(30) Foreign Application Priority Data

Sep. 15, 2000 (DE) .................................. 100 45 591

(51) Int. Cl.
| | | |
|---|---|---|
| *A61K 39/395* | (2006.01) | |
| *C07K 16/46* | (2006.01) | |
| *C07K 16/30* | (2006.01) | |
| *B82Y 5/00* | (2011.01) | |
| *A61K 47/48* | (2006.01) | |
| *C07K 14/525* | (2006.01) | |
| *C07K 14/705* | (2006.01) | |

(52) U.S. Cl.
CPC ............. *B82Y 5/00* (2013.01); *A61K 47/48761* (2013.01); *C07K 14/525* (2013.01); *C07K 14/70575* (2013.01); *C07K 2319/00* (2013.01)
USPC ..................... 424/134.1; 424/85.1; 424/133.1; 424/135.1; 530/391.1; 530/391.3; 530/391.5; 530/391.7; 530/391.9

(58) Field of Classification Search
USPC .................... 530/387.1, 387.3, 388.1, 388.22, 530/388.75, 391.1, 391.3, 391.5, 391.7, 530/391.9; 424/130.1, 133.1, 134.1, 135.1, 424/141.1, 143.1, 154.1, 85.1
See application file for complete search history.

(56) References Cited

U.S. PATENT DOCUMENTS 6,046,310 A * 4/2000 Queen et al.
6,455,677 B1 * 9/2002 Park et al. ................. 530/388.85
2003/0044423 A1 * 3/2003 Gillies et al.

OTHER PUBLICATIONS

Xiang et al. Journal of Biotechnology, 53:3-12, 1997.*
Bird et al. Science 242(4877):423-426, Oct. 21, 1988.*
Ashkenazi, et al, "Safety and antitumor activity of recombinant soluble Apo2 ligand", *J Clin Invest*, 104(2), (Jul. 1999), pp. 155-162.
Hu, et al., "Minibody: A novel engineered anti-carcinoembryonic antigen antibody fragment (single-chain Fv-CH3) which exhibits rapid, high-level targeting of xenografts", *Cancer Res*, 56(13), (Jul. 1996), pp. 3055-3061.
Jo, et al., "Chemotaxis of primitive hematopoietic cells in response to stromal cell-derived factor-1", *J Clin Invest.*, 105(1). (Jan. 2000), pp. 101-111.
Ogasawara, et al., "Lethal effect of the anti-Fas antibody in mice", *Nature*, 364(6440); Erratum in: Nature Oct. 7, 1993, (Aug. 26, 1993) , pp. 806-809.
Pitti, et al., "Induction of apoptosis by Apo-2 ligand, a new member of the tumor necrosis factor cytokine family", *J Biol Chem.*, 271(22), (May 31, 1996), pp. 12687-12690.
Rippmann, et al., "Fusion of the tissue factor extracellular domain to a tumour stroma specific single-chain fragment variable antibody results in an antigen-specific coagulation-promoting molecule"., *Biochem J.*, 349 Pt 3, (Aug. 1, 2000), pp. 805-812.
Schneider, et al., "Conversion of membrane-bound Fas(CD95) ligand to its soluble form is associated with downregulation of its proapoptotic activity and loss of liver toxicity", *J Exp Med.*, 187(8), (Apr. 20, 1998), pp. 1205-1213.
Walczek, et al., "Tumoricidal activity of tumor necrosis factor-related apoptosis-inducing ligand in vivo", *Nat Med.*, 5(2), (Feb. 1999), pp. 157-163.
Wiley, et al., "Identification and characterization of a new member of the TNF family that induces apoptosis", 3(6), (Dec. 1995), pp. 673-682.
Holler, Nils, et al., "Two Adjacent Trimeric Fas Ligands Are Required for Fas Signaling and Formation of a Death-Inducing Signaling Complex", *Molecular and Cellular Biology*, vol. 23, No. 4, (Feb. 2003), 1428-1440
Brocks, Bodo , et al., "A TNF receptor antagonistic scFv, which is not secreted in mammalian cells, is expressed as a soluble mono- and bivalent scFv derivative in insect cells", *Immunotechnolooy* 3(3), (Oct. 1997),173-184.
Brocks, Bodo , et al., "Species-crossreactive scFv against the tumor stroma marker "fibroblast activation protein" selected by phage display from an immunized FAP-/-knock-out mouse", *Molecular Medicine* 7(7), (Jul. 2001),461-469.

(Continued)

*Primary Examiner* — Ram R Shukla
*Assistant Examiner* — Anne Holleran
(74) *Attorney, Agent, or Firm* — Schwegman Lundberg & Woessner, P.A.

(57) ABSTRACT

Subject matter of the invention are antibody-cytokine fusion proteins having proapoptotic and immune modulating properties, but wherein the cytokine moiety a priori has a bioactivity which is very low or restricted to certain receptor subtypes. These reagent exert their full biological activity via the corresponding cytokine receptor(s) only after antibody-mediated binding of the fusion protein to a specific cell membrane-expressed target molecule. By suitable choice of the antibody specificity, the cytokine activity is directed to the tissue, e.g. tumor tissue, to be treated, and a therapeutic agent can be produced being specifically designed/optimized for the respective indication/tumor entity.

3 Claims, 3 Drawing Sheets

(56) References Cited

OTHER PUBLICATIONS

Figure 1:
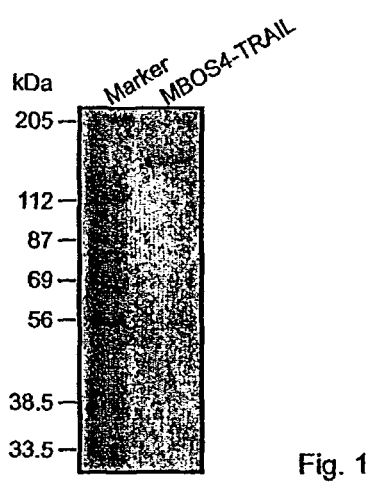

Ichikawa, Kimihisa, et al., "Tumoricidal activity of a novel anti-human DR5 monoclonal antibody without hepatocyte cytotoxicity", *Nature Medicine*, vol. 7, No. 8, (Aug. 2001), 954-960.

Mersmann, Michael, et al., "Human antibody derivatives against the fibroblast activation protein for tumor stroma targeting of carcinomas", *Int. J. Cancer*, vol. 92, (Apr. 15, 2001), 240-248.

Wuest, Thomas, "'Fibroblast activation protein' spezifische rekombinante Antikorperderivate zur Tumordetektion und Therapie", (2001), 1-93.

\* cited by examiner

| Code letter | Construct Scheme | Name |
|---|---|---|
| A | L – OS4 (anti-FAP) –L1– CH3 –L2– TRAIL(95-281) | TRAIL-AMAIZe(MBOS4) |
| B | L – OS4 (anti-FAP) – TRAIL(95-281) | TRAIL-AMAIZe(OS4) |
| C | L – 40 (anti-FAP) – TRAIL(95-281) | TRAIL-AMAIZe(40) |
| D | L – 40 (anti-FAP) – FasL(139-281) | FasL-AMAIZe(40) |
| E | L – OS4 (anti-FAP) – FasL(139-281) | FasL-AMAIZe(OS4) |
| F | L – 40 (anti-FAP) – Flag – FasL(139-281) | FasL-AMAIZe(40-Flag) |

Fig. 3

SEQUENCE LISTING

```
<160> NUMBER OF SEQ ID NOS: 29

<210> SEQ ID NO 1
<211> LENGTH: 1845
<212> TYPE: DNA
<213> ORGANISM: Artificial Sequence
<220> FEATURE:
<223> OTHER INFORMATION: Synthetic coding DNA sequence (upper line,
      coding DNA strand, nucleotide 1-1845) and translated amino acid
      (AA) sequence (lower line, AA 1-614) of an anti-body-cytokine
      AMAIZe fusion protein
<220> FEATURE:
<221> NAME/KEY: CDS
<222> LOCATION: (1)..(1845)
<220> FEATURE:
<223> OTHER INFORMATION: Sequence of leader peptide: NT 1-57, AA 1-19
<220> FEATURE:
<223> OTHER INFORMATION: Sequence of the single chain (scFv) antibody
      fragment OS4 (specific for the tumor stroma antigen FAP): NT
      58-822, AA 20-274
<220> FEATURE:
<223> OTHER INFORMATION: Sequence of linker 1 (L1) between scFv and
      immunoglobulin-CH3 domain: NT 823-942, AA 275-314
<220> FEATURE:
<223> OTHER INFORMATION: Sequence of the immunoglobulin-CH3 domain: NT
      943-1254, AA 315-418
<220> FEATURE:
<223> OTHER INFORMATION: Sequence of linker 2 between Ig CH3 domain and
      TRAIL: NT 1254-1281, AA 419-427
<220> FEATURE:
<223> OTHER INFORMATION: Sequence of the human TRAIL fragment
      (extracellular domain, from AA 95-281 of the natural human TRAIL
      molecule): NT 1282-1842, AA 428-614
<220> FEATURE:
<223> OTHER INFORMATION: Stop codon: NT 1843-1845

<400> SEQUENCE: 1 atg gac tgg acc tgg cgc gtg ttt tgc ctg ctc gcc gtg gct cct ggg      48
Met Asp Trp Thr Trp Arg Val Phe Cys Leu Leu Ala Val Ala Pro Gly
 1               5                  10                  15 gcc cac agc cag gtg caa cta gtg cag tcc ggc gcc gaa gtg aag aaa      96
Ala His Ser Gln Val Gln Leu Val Gln Ser Gly Ala Glu Val Lys Lys
             20                  25                  30 ccc ggt gct tcc gtg aaa gtc agc tgt aaa act agt aga tac acc ttc     144
Pro Gly Ala Ser Val Lys Val Ser Cys Lys Thr Ser Arg Tyr Thr Phe
         35                  40                  45 act gaa tac acc ata cac tgg gtt aga cag gcc cct ggc caa agg ctg     192
Thr Glu Tyr Thr Ile His Trp Val Arg Gln Ala Pro Gly Gln Arg Leu
     50                  55                  60 gag tgg ata gga ggt att aat cct aac aat ggt att cct aac tac aac     240
Glu Trp Ile Gly Gly Ile Asn Pro Asn Asn Gly Ile Pro Asn Tyr Asn
 65                  70                  75                  80 cag aag ttc aag ggc cgg gtc acc atc acc gta gac acc tct gcc agc     288
Gln Lys Phe Lys Gly Arg Val Thr Ile Thr Val Asp Thr Ser Ala Ser
                 85                  90                  95 acc gcc tac atg gaa ctg tcc agc ctg cgc tcc gag gac act gca gtc     336
Thr Ala Tyr Met Glu Leu Ser Ser Leu Arg Ser Glu Asp Thr Ala Val
            100                 105                 110 tac tac tgc gcc aga aga aga atc gcc tat ggt tac gac gag ggc cat     384
Tyr Tyr Cys Ala Arg Arg Arg Ile Ala Tyr Gly Tyr Asp Glu Gly His
        115                 120                 125 gct atg gac tac tgg ggt caa gga acc ctt gtc acc gtc tcc tca gcc     432
Ala Met Asp Tyr Trp Gly Gln Gly Thr Leu Val Thr Val Ser Ser Ala
    130                 135                 140
```

```
tcc acc aag ggc cca aag ctt gaa gaa ggt gaa ttt tca gaa gca cgc        480
Ser Thr Lys Gly Pro Lys Leu Glu Glu Gly Glu Phe Ser Glu Ala Arg
145                 150                 155                 160 gta gac att gtg atg acc caa tct cca gac tct ttg gct gtg tct cta        528
Val Asp Ile Val Met Thr Gln Ser Pro Asp Ser Leu Ala Val Ser Leu
                165                 170                 175 ggg gag agg gcc acc atc aac tgc aag tcc agt cag agc ctt tta tat        576
Gly Glu Arg Ala Thr Ile Asn Cys Lys Ser Ser Gln Ser Leu Leu Tyr
            180                 185                 190 tct aga aat caa aag aac tac ttg gcc tgg tat cag cag aaa cca gga        624
Ser Arg Asn Gln Lys Asn Tyr Leu Ala Trp Tyr Gln Gln Lys Pro Gly
        195                 200                 205 cag cca ccc aaa ctc ctc atc ttt tgg gct agc act agg gaa tct ggg        672
Gln Pro Pro Lys Leu Leu Ile Phe Trp Ala Ser Thr Arg Glu Ser Gly
    210                 215                 220 gta cct gat agg ttc agt ggc agt ggg ttt ggg aca gac ttc acc ctc        720
Val Pro Asp Arg Phe Ser Gly Ser Gly Phe Gly Thr Asp Phe Thr Leu
225                 230                 235                 240 acc att agc agc ctg cag gct gaa gat gtg gca gtt tat tac tgt cag        768
Thr Ile Ser Ser Leu Gln Ala Glu Asp Val Ala Val Tyr Tyr Cys Gln
                245                 250                 255 caa tat ttt agc tat ccg ctc acg ttc gga caa ggg acc aag gtg gaa        816
Gln Tyr Phe Ser Tyr Pro Leu Thr Phe Gly Gln Gly Thr Lys Val Glu
            260                 265                 270 ata aaa cgt act gtg gct gca cca tct gtc ttc gct gtc ttc gcg gcc        864
Ile Lys Arg Thr Val Ala Ala Pro Ser Val Phe Ala Val Phe Ala Ala
        275                 280                 285 gca gtt gag ccc aaa tct tgt gac aaa act cac aca tgc cca cca tgc        912
Ala Val Glu Pro Lys Ser Cys Asp Lys Thr His Thr Cys Pro Pro Cys
    290                 295                 300 gga gga gga agt agc gga gga gga tca gga ggg cag ccc cga gaa cca        960
Gly Gly Gly Ser Ser Gly Gly Gly Ser Gly Gly Gln Pro Arg Glu Pro
305                 310                 315                 320 cag gtg tac acc ctg ccc cca tcc cgg gag gag atg acc aag aac cag       1008
Gln Val Tyr Thr Leu Pro Pro Ser Arg Glu Glu Met Thr Lys Asn Gln
                325                 330                 335 gtc agc ctg acc tgc ctg gtc aaa ggc ttc tat ccc agc gac atc gcc       1056
Val Ser Leu Thr Cys Leu Val Lys Gly Phe Tyr Pro Ser Asp Ile Ala
            340                 345                 350 gtg gag tgg gag agc aat ggg cag ccg gag aac aac tac aag acc acg       1104
Val Glu Trp Glu Ser Asn Gly Gln Pro Glu Asn Asn Tyr Lys Thr Thr
        355                 360                 365 cct ccc gtg ctg gac tcc gac ggc tcc ttc ttc ctc tat agc aag ctc       1152
Pro Pro Val Leu Asp Ser Asp Gly Ser Phe Phe Leu Tyr Ser Lys Leu
    370                 375                 380 acc gtg gac aag agc agg tgg cag cag ggg aac gtc ttc tca tgc tcc       1200
Thr Val Asp Lys Ser Arg Trp Gln Gln Gly Asn Val Phe Ser Cys Ser
385                 390                 395                 400 gtg atg cat gag gct ctg cac aac cac tac acg cag aag agc ctc tcc       1248
Val Met His Glu Ala Leu His Asn His Tyr Thr Gln Lys Ser Leu Ser
                405                 410                 415 ctg tcc gga ggt ggc ggt acc gga ggt ggg tct acc tct gag gaa acc       1296
Leu Ser Gly Gly Gly Gly Thr Gly Gly Gly Ser Thr Ser Glu Glu Thr
            420                 425                 430 att tct aca gtt caa gaa aag caa caa aat att tct ccc cta gtg aga       1344
Ile Ser Thr Val Gln Glu Lys Gln Gln Asn Ile Ser Pro Leu Val Arg
        435                 440                 445 gaa aga ggt cct cag aga gta gca gct cac ata act ggg acc aga gga       1392
Glu Arg Gly Pro Gln Arg Val Ala Ala His Ile Thr Gly Thr Arg Gly
```

```
                  450                 455                 460
aga  agc  aac  aca  ttg  tct  tct  cca  aac  tcc  aag  aat  gaa  aag  gct  ctg     1440
Arg  Ser  Asn  Thr  Leu  Ser  Ser  Pro  Asn  Ser  Lys  Asn  Glu  Lys  Ala  Leu
465                 470                 475                 480 ggc  cgc  aaa  ata  aac  tcc  tgg  gaa  tca  tca  agg  agt  ggg  cat  tca  ttc     1488
Gly  Arg  Lys  Ile  Asn  Ser  Trp  Glu  Ser  Ser  Arg  Ser  Gly  His  Ser  Phe
                    485                 490                 495 ctg  agc  aac  ttg  cac  ttg  agg  aat  ggt  gaa  ctg  gtc  atc  cat  gaa  aaa     1536
Leu  Ser  Asn  Leu  His  Leu  Arg  Asn  Gly  Glu  Leu  Val  Ile  His  Glu  Lys
               500                 505                 510 ggg  ttt  tac  tac  atc  tat  tcc  caa  aca  tac  ttt  cga  ttt  cag  gag  gaa     1584
Gly  Phe  Tyr  Tyr  Ile  Tyr  Ser  Gln  Thr  Tyr  Phe  Arg  Phe  Gln  Glu  Glu
               515                 520                 525 ata  aaa  gaa  aac  aca  aag  aac  gac  aaa  caa  atg  gtc  caa  tat  att  tac     1632
Ile  Lys  Glu  Asn  Thr  Lys  Asn  Asp  Lys  Gln  Met  Val  Gln  Tyr  Ile  Tyr
530                 535                 540 aaa  tac  aca  agt  tat  cct  gac  cct  ata  ttg  ttg  atg  aaa  agt  gct  aga     1680
Lys  Tyr  Thr  Ser  Tyr  Pro  Asp  Pro  Ile  Leu  Leu  Met  Lys  Ser  Ala  Arg
545                 550                 555                 560 aat  agt  tgt  tgg  tct  aaa  gat  gca  gaa  tat  gga  ctc  tat  tcc  atc  tat     1728
Asn  Ser  Cys  Trp  Ser  Lys  Asp  Ala  Glu  Tyr  Gly  Leu  Tyr  Ser  Ile  Tyr
                    565                 570                 575 caa  ggg  gga  ata  ttt  gag  ctt  aag  gaa  aat  gac  aga  att  ttt  gtt  tct     1776
Gln  Gly  Gly  Ile  Phe  Glu  Leu  Lys  Glu  Asn  Asp  Arg  Ile  Phe  Val  Ser
               580                 585                 590 gta  aca  aat  gag  cac  ttg  ata  gac  atg  gac  cat  gaa  gcc  agt  ttt  ttc     1824
Val  Thr  Asn  Glu  His  Leu  Ile  Asp  Met  Asp  His  Glu  Ala  Ser  Phe  Phe
               595                 600                 605 ggg  gcc  ttt  tta  gtt  ggc  taa                                                  1845
Gly  Ala  Phe  Leu  Val  Gly
          610
```

<210> SEQ ID NO 2
<211> LENGTH: 614
<212> TYPE: PRT
<213> ORGANISM: Artificial Sequence
<220> FEATURE:
<223> OTHER INFORMATION: Synthetic amino acid sequence of an anti-body-
      cytokine AMAIZe fusion protein of the invention exemplified by
      TRAIL-AMAIZe (MBOS4)
<220> FEATURE:
<223> OTHER INFORMATION: Stop codon: NT 1843-1845

<400> SEQUENCE: 2

```
Met  Asp  Trp  Thr  Trp  Arg  Val  Phe  Cys  Leu  Leu  Ala  Val  Ala  Pro  Gly
  1                   5                  10                  15

Ala  His  Ser  Gln  Val  Gln  Leu  Val  Gln  Ser  Gly  Ala  Glu  Val  Lys  Lys
                 20                  25                  30

Pro  Gly  Ala  Ser  Val  Lys  Val  Ser  Cys  Lys  Thr  Ser  Tyr  Thr  Phe
             35                  40                  45

Thr  Glu  Tyr  Thr  Ile  His  Trp  Val  Arg  Gln  Ala  Pro  Gly  Gln  Arg  Leu
         50                  55                  60

Glu  Trp  Ile  Gly  Gly  Ile  Asn  Pro  Asn  Asn  Gly  Ile  Pro  Asn  Tyr  Asn
 65                  70                  75                  80

Gln  Lys  Phe  Lys  Gly  Arg  Val  Thr  Ile  Thr  Val  Asp  Thr  Ser  Ala  Ser
                 85                  90                  95

Thr  Ala  Tyr  Met  Glu  Leu  Ser  Ser  Leu  Arg  Ser  Glu  Asp  Thr  Ala  Val
                100                 105                 110

Tyr  Tyr  Cys  Ala  Arg  Arg  Ile  Ala  Tyr  Gly  Tyr  Asp  Glu  Gly  His
            115                 120                 125
```

```
Ala Met Asp Tyr Trp Gly Gln Gly Thr Leu Val Thr Val Ser Ser Ala
    130                 135                 140
Ser Thr Lys Gly Pro Lys Leu Glu Glu Gly Glu Phe Ser Glu Ala Arg
145                 150                 155                 160
Val Asp Ile Val Met Thr Gln Ser Pro Asp Ser Leu Ala Val Ser Leu
            165                 170                 175
Gly Glu Arg Ala Thr Ile Asn Cys Lys Ser Ser Gln Ser Leu Leu Tyr
                180                 185                 190
Ser Arg Asn Gln Lys Asn Tyr Leu Ala Trp Tyr Gln Gln Lys Pro Gly
        195                 200                 205
Gln Pro Pro Lys Leu Leu Ile Phe Trp Ala Ser Thr Arg Glu Ser Gly
    210                 215                 220
Val Pro Asp Arg Phe Ser Gly Ser Gly Phe Gly Thr Asp Phe Thr Leu
225                 230                 235                 240
Thr Ile Ser Ser Leu Gln Ala Glu Asp Val Ala Val Tyr Tyr Cys Gln
            245                 250                 255
Gln Tyr Phe Ser Tyr Pro Leu Thr Phe Gly Gln Gly Thr Lys Val Glu
                260                 265                 270
Ile Lys Arg Thr Val Ala Ala Pro Ser Val Phe Ala Val Phe Ala Ala
        275                 280                 285
Ala Val Glu Pro Lys Ser Cys Asp Lys Thr His Thr Cys Pro Pro Cys
    290                 295                 300
Gly Gly Gly Ser Ser Gly Gly Ser Gly Gly Gln Pro Arg Glu Pro
305                 310                 315                 320
Gln Val Tyr Thr Leu Pro Pro Ser Arg Glu Glu Met Thr Lys Asn Gln
                325                 330                 335
Val Ser Leu Thr Cys Leu Val Lys Gly Phe Tyr Pro Ser Asp Ile Ala
        340                 345                 350
Val Glu Trp Glu Ser Asn Gly Gln Pro Glu Asn Asn Tyr Lys Thr Thr
    355                 360                 365
Pro Pro Val Leu Asp Ser Asp Gly Ser Phe Phe Leu Tyr Ser Lys Leu
370                 375                 380
Thr Val Asp Lys Ser Arg Trp Gln Gln Gly Asn Val Phe Ser Cys Ser
385                 390                 395                 400
Val Met His Glu Ala Leu His Asn His Tyr Thr Gln Lys Ser Leu Ser
            405                 410                 415
Leu Ser Gly Gly Gly Thr Gly Gly Ser Thr Ser Glu Glu Thr
                420                 425                 430
Ile Ser Thr Val Gln Glu Lys Gln Gln Asn Ile Ser Pro Leu Val Arg
        435                 440                 445
Glu Arg Gly Pro Gln Arg Val Ala Ala His Ile Thr Gly Thr Arg Gly
    450                 455                 460
Arg Ser Asn Thr Leu Ser Ser Pro Asn Ser Lys Asn Glu Lys Ala Leu
465                 470                 475                 480
Gly Arg Lys Ile Asn Ser Trp Glu Ser Ser Arg Ser Gly His Ser Phe
            485                 490                 495
Leu Ser Asn Leu His Leu Arg Asn Gly Glu Leu Val Ile His Glu Lys
                500                 505                 510
Gly Phe Tyr Tyr Ile Tyr Ser Gln Thr Tyr Phe Arg Phe Gln Glu Glu
        515                 520                 525
Ile Lys Glu Asn Thr Lys Asn Asp Lys Gln Met Val Gln Tyr Ile Tyr
    530                 535                 540
```

```
Lys Tyr Thr Ser Tyr Pro Asp Pro Ile Leu Leu Met Lys Ser Ala Arg
545                 550                 555                 560

Asn Ser Cys Trp Ser Lys Asp Ala Glu Tyr Gly Leu Tyr Ser Ile Tyr
            565                 570                 575

Gln Gly Gly Ile Phe Glu Leu Lys Glu Asn Asp Arg Ile Phe Val Ser
            580                 585                 590

Val Thr Asn Glu His Leu Ile Asp Met Asp His Glu Ala Ser Phe Phe
        595                 600                 605

Gly Ala Phe Leu Val Gly
        610

<210> SEQ ID NO 3
<211> LENGTH: 1443
<212> TYPE: DNA
<213> ORGANISM: Artificial Sequence
<220> FEATURE:
<223> OTHER INFORMATION: Synthetic coding DNA sequence (upper line,
      coding DNA strand, nucleotide (NT) 1-1443) and translated amino
      acid (AA) sequence (upper line, AA 1-480) of an anti-body-cytokine
      AMAIZe fusion protein
<220> FEATURE:
<221> NAME/KEY: CDS
<222> LOCATION: (1)..(1443)
<220> FEATURE:
<223> OTHER INFORMATION: Sequence of leader peptide: NT 1-57, AA 1-19
<220> FEATURE:
<223> OTHER INFORMATION: Sequence of the single chain (scFv) antibody
      fragment OS4 (specific for the tumor stroma antigen FAP): NT
      58-822, AA 20-274
<220> FEATURE:
<223> OTHER INFORMATION: Sequence of the linker between scFv and the
      TRAIL fragment (AA 95-281): NT 823-879, AA 275-293
<220> FEATURE:
<223> OTHER INFORMATION: Sequence of the human TRAIL fragment
      (extracellular domain, AA 95-281 of the natural human TRAIL
      molecule): NT 880-1440 AA 294-480
<220> FEATURE:
<223> OTHER INFORMATION: Stop codon: NT 1441-1443

<400> SEQUENCE: 3 atg gac tgg acc tgg cgc gtg ttt tgc ctg ctc gcc gtg gct cct ggg    48
Met Asp Trp Thr Trp Arg Val Phe Cys Leu Leu Ala Val Ala Pro Gly
1               5                   10                  15 gcc cac agc cag gtg caa cta gtg cag tcc ggc gcc gaa gtg aag aaa    96
Ala His Ser Gln Val Gln Leu Val Gln Ser Gly Ala Glu Val Lys Lys
                20                  25                  30 ccc ggt gct tcc gtg aaa gtc agc tgt aaa act agt aga tac acc ttc   144
Pro Gly Ala Ser Val Lys Val Ser Cys Lys Thr Ser Arg Tyr Thr Phe
        35                  40                  45 act gaa tac acc ata cac tgg gtt aga cag gcc cct ggc caa agg ctg   192
Thr Glu Tyr Thr Ile His Trp Val Arg Gln Ala Pro Gly Gln Arg Leu
    50                  55                  60 gag tgg ata gga ggt att aat cct aac aat ggt att cct aac tac aac   240
Glu Trp Ile Gly Gly Ile Asn Pro Asn Asn Gly Ile Pro Asn Tyr Asn
65                  70                  75                  80 cag aag ttc aag ggc cgg gtc acc atc acc gta gac acc tct gcc agc   288
Gln Lys Phe Lys Gly Arg Val Thr Ile Thr Val Asp Thr Ser Ala Ser
                85                  90                  95 acc gcc tac atg gaa ctg tcc agc ctg cgc tcc gag gac act gca gtc   336
Thr Ala Tyr Met Glu Leu Ser Ser Leu Arg Ser Glu Asp Thr Ala Val
                100                 105                 110 tac tac tgc gcc aga aga aga atc gcc tat ggt tac gac gag ggc cat   384
Tyr Tyr Cys Ala Arg Arg Arg Ile Ala Tyr Gly Tyr Asp Glu Gly His
        115                 120                 125 gct atg gac tac tgg ggt caa gga acc ctt gtc acc gtc tcc tca gcc   432
```

```
            Ala Met Asp Tyr Trp Gly Gln Gly Thr Leu Val Thr Val Ser Ser Ala
                130             135             140 tcc acc aag ggc cca aag ctt gaa gaa ggt gaa ttt tca gaa gca cgc        480
Ser Thr Lys Gly Pro Lys Leu Glu Glu Gly Glu Phe Ser Glu Ala Arg
145             150             155             160 gta gac att gtg atg acc caa tct cca gac tct ttg gct gtg tct cta        528
Val Asp Ile Val Met Thr Gln Ser Pro Asp Ser Leu Ala Val Ser Leu
                165             170             175 ggg gag agg gcc acc atc aac tgc aag tcc agt cag agc ctt tta tat        576
Gly Glu Arg Ala Thr Ile Asn Cys Lys Ser Ser Gln Ser Leu Leu Tyr
            180             185             190 tct aga aat caa aag aac tac ttg gcc tgg tat cag cag aaa cca gga        624
Ser Arg Asn Gln Lys Asn Tyr Leu Ala Trp Tyr Gln Gln Lys Pro Gly
        195             200             205 cag cca ccc aaa ctc ctc atc ttt tgg gct agc act agg gaa tct ggg        672
Gln Pro Pro Lys Leu Leu Ile Phe Trp Ala Ser Thr Arg Glu Ser Gly
    210             215             220 gta cct gat agg ttc agt ggc agt ggg ttt ggg aca gac ttc acc ctc        720
Val Pro Asp Arg Phe Ser Gly Ser Gly Phe Gly Thr Asp Phe Thr Leu
225             230             235             240 acc att agc agc ctg cag gct gaa gat gtg gca gtt tat tac tgt cag        768
Thr Ile Ser Ser Leu Gln Ala Glu Asp Val Ala Val Tyr Tyr Cys Gln
                245             250             255 caa tat ttt agc tat ccg ctc acg ttc gga caa ggg acc aag gtg gaa        816
Gln Tyr Phe Ser Tyr Pro Leu Thr Phe Gly Gln Gly Thr Lys Val Glu
                260             265             270 ata aaa cgt act gtg gct gca cca tct gtc ttc gct gtc ttc gcg gcc        864
Ile Lys Arg Thr Val Ala Ala Pro Ser Val Phe Ala Val Phe Ala Ala
            275             280             285 gca gtt gag ctc gag acc tct gag gaa acc att tct aca gtt caa gaa        912
Ala Val Glu Leu Glu Thr Ser Glu Glu Thr Ile Ser Thr Val Gln Glu
        290             295             300 aag caa caa aat att tct ccc cta gtg aga gaa aga ggt cct cag aga        960
Lys Gln Gln Asn Ile Ser Pro Leu Val Arg Glu Arg Gly Pro Gln Arg
305             310             315             320 gta gca gct cac ata act ggg acc aga gga aga agc aac aca ttg tct       1008
Val Ala Ala His Ile Thr Gly Thr Arg Gly Arg Ser Asn Thr Leu Ser
                325             330             335 tct cca aac tcc aag aat gaa aag gct ctg ggc cgc aaa ata aac tcc       1056
Ser Pro Asn Ser Lys Asn Glu Lys Ala Leu Gly Arg Lys Ile Asn Ser
                340             345             350 tgg gaa tca tca agg agt ggg cat tca ttc ctg agc aac ttg cac ttg       1104
Trp Glu Ser Ser Arg Ser Gly His Ser Phe Leu Ser Asn Leu His Leu
            355             360             365 agg aat ggt gaa ctg gtc atc cat gaa aaa ggg ttt tac tac atc tat       1152
Arg Asn Gly Glu Leu Val Ile His Glu Lys Gly Phe Tyr Tyr Ile Tyr
370             375             380 tcc caa aca tac ttt cga ttt cag gag gaa ata aaa gaa aac aca aag       1200
Ser Gln Thr Tyr Phe Arg Phe Gln Glu Glu Ile Lys Glu Asn Thr Lys
                390             395             400
385 aac gac aaa caa atg gtc caa tat att tac aaa tac aca agt tat cct       1248
Asn Asp Lys Gln Met Val Gln Tyr Ile Tyr Lys Tyr Thr Ser Tyr Pro
                405             410             415 gac cct ata ttg ttg atg aaa agt gct aga aat agt tgt tgg tct aaa       1296
Asp Pro Ile Leu Leu Met Lys Ser Ala Arg Asn Ser Cys Trp Ser Lys
            420             425             430 gat gca gaa tat gga ctc tat tcc atc tat caa ggg gga ata ttt gag       1344
Asp Ala Glu Tyr Gly Leu Tyr Ser Ile Tyr Gln Gly Gly Ile Phe Glu
        435             440             445
```

```
ctt aag gaa aat gac aga att ttt gtt tct gta aca aat gag cac ttg      1392
Leu Lys Glu Asn Asp Arg Ile Phe Val Ser Val Thr Asn Glu His Leu
    450             455                 460 ata gac atg gac cat gaa gcc agt ttt ttc ggg gcc ttt tta gtt ggc      1440
Ile Asp Met Asp His Glu Ala Ser Phe Phe Gly Ala Phe Leu Val Gly
465             470                 475                 480 taa                                                                  1443
```

<210> SEQ ID NO 4
<211> LENGTH: 480
<212> TYPE: PRT
<213> ORGANISM: Artificial Sequence
<220> FEATURE:
<223> OTHER INFORMATION: Synthetic amino acid sequence of an anti-body-
      cytokine AMAIZe fusion protein of the invention exemplified by
      TRAIL-AMAIZe (OS4)
<220> FEATURE:
<223> OTHER INFOR

```
                    290                 295                 300
Lys Gln Gln Asn Ile Ser Pro Leu Val Arg Glu Arg Gly Pro Gln Arg
305                 310                 315                 320

Val Ala Ala His Ile Thr Gly Thr Arg Gly Arg Ser Asn Thr Leu Ser
                325                 330                 335

Ser Pro Asn Ser Lys Asn Glu Lys Ala Leu Gly Arg Lys Ile Asn Ser
            340                 345                 350

Trp Glu Ser Ser Arg Ser Gly His Ser Phe Leu Ser Asn Leu His Leu
        355                 360                 365

Arg Asn Gly Glu Leu Val Ile His Glu Lys Gly Phe Tyr Tyr Ile Tyr
    370                 375                 380

Ser Gln Thr Tyr Phe Arg Phe Gln Glu Glu Ile Lys Glu Asn Thr Lys
385                 390                 395                 400

Asn Asp Lys Gln Met Val Gln Tyr Ile Tyr Lys Tyr Thr Ser Tyr Pro
                405                 410                 415

Asp Pro Ile Leu Leu Met Lys Ser Ala Arg Asn Ser Cys Trp Ser Lys
            420                 425                 430

Asp Ala Glu Tyr Gly Leu Tyr Ser Ile Tyr Gln Gly Gly Ile Phe Glu
        435                 440                 445

Leu Lys Glu Asn Asp Arg Ile Phe Val Ser Val Thr Asn Glu His Leu
    450                 455                 460

Ile Asp Met Asp His Glu Ala Ser Phe Phe Gly Ala Phe Leu Val Gly
465                 470                 475                 480
```

<210> SEQ ID NO 5
<211> LENGTH: 1386
<212> TYPE: DNA
<213> ORGANISM: Artificial Sequence
<220> FEATURE:
<223> OTHER INFORMATION: Synthetic coding DNA sequence (upper line, coding DNA strand, nucleotide (NT) 1-1386) and translated amino acid (AA) sequence (lower line, AA 1-461) of an anti-body-cytokine AMAIZe fusion protein
<220> FEATURE:
<221> NAME/KEY: CDS
<222> LOCATION: (1)..(1386)
<220> FEATURE:
<223> OTHER INFORMATION: Sequence of leader peptide: NT 1-57, AA 1-19
<220> FEATURE:
<223> OTHER INFORMATION: Sequence of the single chain (scFv) antibody fragment 40 (specific for the tumor stroma antigen FAP): NT 58-801, AA 20-267
<220> FEATURE:
<223> OTHER INFORMATION: Sequence of the linker between scFv and the TRAIL fragment (AA 95-281): NT 802-822, AA 268-274
<220> FEATURE:
<223> OTHER INFORMATION: Sequence of the human TRAIL fragment (extracellular domain, AA 95-281 of the natural human TRAIL molecule): NT 823-1383, AA 275-461
<220> FEATURE:
<223> OTHER INFORMATION: Stop codon: NT 1384-1386

<400> SEQUENCE: 5

```
atg gac tgg acc tgg cgc gtg ttt tgc ctg ctc gcc gtg gct cct ggg    48
Met Asp Trp Thr Trp Arg Val Phe Cys Leu Leu Ala Val Ala Pro Gly
1               5                   10                  15 gcc cac agc cag gta cag ctg gtg cag tct ggg gga ggc atg gta gag    96
Ala His Ser Gln Val Gln Leu Val Gln Ser Gly Gly Gly Met Val Glu
            20                  25                  30 cct ggg ggg tcc ctt aga ctc tcc tgt gca gcc tct gga ttc act ttc   144
Pro Gly Gly Ser Leu Arg Leu Ser Cys Ala Ala Ser Gly Phe Thr Phe
        35                  40                  45 agt aat gcc tgg atg agc tgg gtc cgc cag gct cca ggg aag ggg ctg   192
```

```
Ser Asn Ala Trp Met Ser Trp Val Arg Gln Ala Pro Gly Lys Gly Leu
     50                  55                  60 gag tgg gtt ggc cgt ata aaa agc aaa gct ggt ggg aca gca gag        240
Glu Trp Val Gly Arg Ile Lys Ser Lys Ala Gly Gly Thr Ala Glu
 65                  70                  75                  80 tac gct gca ccc gtg aaa ggc aga ttc acc atc tca aga gat gat tca   288
Tyr Ala Ala Pro Val Lys Gly Arg Phe Thr Ile Ser Arg Asp Asp Ser
                     85                  90                  95 caa aac acg ctg tat ctg caa atg aac agc ctg aaa acc gac gac aca   336
Gln Asn Thr Leu Tyr Leu Gln Met Asn Ser Leu Lys Thr Asp Asp Thr
                100                 105                 110 gcc gtg tat tac tgt acc aca cat gtc tac ggt gcc ccc cgg aac tgg   384
Ala Val Tyr Tyr Cys Thr Thr His Val Tyr Gly Ala Pro Arg Asn Trp
            115                 120                 125 ggc cag gga tcc ctg gtc acc gtc tcc tca gcc tcc acc aag ggc cca   432
Gly Gln Gly Ser Leu Val Thr Val Ser Ser Ala Ser Thr Lys Gly Pro
        130                 135                 140 aag ctt gaa gaa ggt gaa ttt tca gaa gca cgc gta cag tct gtg ttg   480
Lys Leu Glu Glu Gly Glu Phe Ser Glu Ala Arg Val Gln Ser Val Leu
145                 150                 155                 160 act cag ccg ccc tca gtg tct gcg gcc cca gga cag aag gtc acc atc   528
Thr Gln Pro Pro Ser Val Ser Ala Ala Pro Gly Gln Lys Val Thr Ile
                165                 170                 175 tcc tgc tct gga agc agc tcc aac att gga aat aat tat gtc tcc tgg   576
Ser Cys Ser Gly Ser Ser Ser Asn Ile Gly Asn Asn Tyr Val Ser Trp
                180                 185                 190 tac gtt caa ctc cca gga aca gcc ccc aaa ctc ctc att tat gac aat   624
Tyr Val Gln Leu Pro Gly Thr Ala Pro Lys Leu Leu Ile Tyr Asp Asn
            195                 200                 205 aat aag cga ttc tca gga gtt cct gac cga ttc tct ggc tcc aag tct   672
Asn Lys Arg Phe Ser Gly Val Pro Asp Arg Phe Ser Gly Ser Lys Ser
        210                 215                 220 ggc acg tca gcc acc ctg ggc atc acc ggg ctc cag act ggg gac gag   720
Gly Thr Ser Ala Thr Leu Gly Ile Thr Gly Leu Gln Thr Gly Asp Glu
225                 230                 235                 240 gcc gat tat tac tgc gga gca tgg gat ggc agc ctg cgt gaa gcg gta   768
Ala Asp Tyr Tyr Cys Gly Ala Trp Asp Gly Ser Leu Arg Glu Ala Val
                245                 250                 255 ttc ggc gga ggg acc aag gtc acc gtc cta ggt gcg gcc gca gtt gag   816
Phe Gly Gly Gly Thr Lys Val Thr Val Leu Gly Ala Ala Ala Val Glu
                260                 265                 270 ctc gag acc tct gag gaa acc att tct aca gtt caa gaa aag caa caa   864
Leu Glu Thr Ser Glu Glu Thr Ile Ser Thr Val Gln Glu Lys Gln Gln
            275                 280                 285 aat att tct ccc cta gtg aga gaa aga ggt cct cag aga gta gca gct   912
Asn Ile Ser Pro Leu Val Arg Glu Arg Gly Pro Gln Arg Val Ala Ala
        290                 295                 300 cac ata act ggg acc aga gga aga agc aac aca ttg tct tct cca aac   960
His Ile Thr Gly Thr Arg Gly Arg Ser Asn Thr Leu Ser Ser Pro Asn
305                 310                 315                 320 tcc aag aat gaa aag gct ctg ggc cgc aaa ata aac tcc tgg gaa tca   1008
Ser Lys Asn Glu Lys Ala Leu Gly Arg Lys Ile Asn Ser Trp Glu Ser
                325                 330                 335 tca agg agt ggg cat tca ttc ctg agc aac ttg cac ttg agg aat ggt   1056
Ser Arg Ser Gly His Ser Phe Leu Ser Asn Leu His Leu Arg Asn Gly
                340                 345                 350 gaa ctg gtc atc cat gaa aaa ggg ttt tac tac atc tat tcc caa aca   1104
Glu Leu Val Ile His Glu Lys Gly Phe Tyr Tyr Ile Tyr Ser Gln Thr
            355                 360                 365
```

```
tac ttt cga ttt cag gag gaa ata aaa gaa aac aca aag aac gac aaa    1152
Tyr Phe Arg Phe Gln Glu Glu Ile Lys Glu Asn Thr Lys Asn Asp Lys
         370                 375                 380 caa atg gtc caa tat att tac aaa tac aca agt tat cct gac cct ata    1200
Gln Met Val Gln Tyr Ile Tyr Lys Tyr Thr Ser Tyr Pro Asp Pro Ile
385                 390                 395                 400 ttg ttg atg aaa agt gct aga aat agt tgt tgg tct aaa gat gca gaa    1248
Leu Leu Met Lys Ser Ala Arg Asn Ser Cys Trp Ser Lys Asp Ala Glu
             405                 410                 415 tat gga ctc tat tcc atc tat caa ggg gga ata ttt gag ctt aag gaa    1296
Tyr Gly Leu Tyr Ser Ile Tyr Gln Gly Gly Ile Phe Glu Leu Lys Glu
                 420                 425                 430 aat gac aga att ttt gtt tct gta aca aat gag cac ttg ata gac atg    1344
Asn Asp Arg Ile Phe Val Ser Val Thr Asn Glu His Leu Ile Asp Met
                     435                 440                 445 gac cat gaa gcc agt ttt ttc ggg gcc ttt tta gtt ggc taa            1386
Asp His Glu Ala Ser Phe Phe Gly Ala Phe Leu Val Gly
                 450                 455                 460
```

<210> SEQ ID NO 6
<211> LENGTH: 461
<212> TYPE: PRT
<213> ORGANISM: Artificial Sequence
<220> FEATURE:
<223> OTHER INFORMATION: Synthetic amino acid sequence of an anti-body-
      cytokine AMAIZe fusion protein of the invention exemplified by
      TRAIL-AMAIZe (40)
<220> FEATURE:
<223> OTHER INFORMATION: Stop codon: NT 1384-1386

<400> SEQUENCE: 6

```
Met Asp Trp Thr Trp Arg Val Phe Cys Leu Leu Ala Val Ala Pro Gly
 1               5                  10                  15

Ala His Ser Gln Val Gln Leu Val Gln Ser Gly Gly Gly Met Val Glu
             20                  25                  30

Pro Gly Gly Ser Leu Arg Leu Ser Cys Ala Ala Ser Gly Phe Thr Phe
         35                  40                  45

Ser Asn Ala Trp Met Ser Trp Val Arg Gln Ala Pro Gly Lys Gly Leu
     50                  55                  60

Glu Trp Val Gly Arg Ile Lys Ser Lys Ala Gly Gly Thr Ala Glu
 65                  70                  75                  80

Tyr Ala Ala Pro Val Lys Gly Arg Phe Thr Ile Ser Arg Asp Asp Ser
                 85                  90                  95

Gln Asn Thr Leu Tyr Leu Gln Met Asn Ser Leu Lys Thr Asp Asp Thr
            100                 105                 110

Ala Val Tyr Tyr Cys Thr Thr His Val Tyr Gly Ala Pro Arg Asn Trp
        115                 120                 125

Gly Gln Gly Ser Leu Val Thr Val Ser Ser Ala Ser Thr Lys Gly Pro
    130                 135                 140

Lys Leu Glu Glu Gly Glu Phe Ser Glu Ala Arg Val Gln Ser Val Leu
145                 150                 155                 160

Thr Gln Pro Pro Ser Val Ser Ala Ala Pro Gly Gln Lys Val Thr Ile
                165                 170                 175

Ser Cys Ser Gly Ser Ser Ser Asn Ile Gly Asn Asn Tyr Val Ser Trp
            180                 185                 190

Tyr Val Gln Leu Pro Gly Thr Ala Pro Lys Leu Leu Ile Tyr Asp Asn
        195                 200                 205

Asn Lys Arg Phe Ser Gly Val Pro Asp Arg Phe Ser Gly Ser Lys Ser
    210                 215                 220
```

Gly Thr Ser Ala Thr Leu Gly Ile Thr Gly Leu Gln Thr Gly Asp Glu
225                 230                 235                 240

Ala Asp Tyr Tyr Cys Gly Ala Trp Asp Gly Ser Leu Arg Glu Ala Val
            245                 250                 255

Phe Gly Gly Gly Thr Lys Val Thr Val Leu Gly Ala Ala Ala Val Glu
        260                 265                 270

Leu Glu Thr Ser Glu Glu Thr Ile Ser Thr Val Gln Glu Lys Gln Gln
    275                 280                 285

Asn Ile Ser Pro Leu Val Arg Glu Arg Gly Pro Gln Arg Val Ala Ala
290                 295                 300

His Ile Thr Gly Thr Arg Gly Arg Ser Asn Thr Leu Ser Ser Pro Asn
305                 310                 315                 320

Ser Lys Asn Glu Lys Ala Leu Gly Arg Lys Ile Asn Ser Trp Glu Ser
            325                 330                 335

Ser Arg Ser Gly His Ser Phe Leu Ser Asn Leu His Leu Arg Asn Gly
        340                 345                 350

Glu Leu Val Ile His Glu Lys Gly Phe Tyr Tyr Ile Tyr Ser Gln Thr
    355                 360                 365

Tyr Phe Arg Phe Gln Glu Glu Ile Lys Glu Asn Thr Lys Asn Asp Lys
370                 375                 380

Gln Met Val Gln Tyr Ile Tyr Lys Tyr Thr Ser Tyr Pro Asp Pro Ile
385                 390                 395                 400

Leu Leu Met Lys Ser Ala Arg Asn Ser Cys Trp Ser Lys Asp Ala Glu
            405                 410                 415

Tyr Gly Leu Tyr Ser Ile Tyr Gln Gly Gly Ile Phe Glu Leu Lys Glu
        420                 425                 430

Asn Asp Arg Ile Phe Val Ser Val Thr Asn Glu His Leu Ile Asp Met
    435                 440                 445

Asp His Glu Ala Ser Phe Phe Gly Ala Phe Leu Val Gly
450                 455                 460

<210> SEQ ID NO 7
<211> LENGTH: 1254
<212> TYPE: DNA
<213> ORGANISM: Artificial Sequence
<220> FEATURE:
<223> OTHER INFORMATION: Synthetic coding DNA sequence (upper line,
      coding DNA strand, nucleotide (NT) 1-1254) and translated amino
      acid (AA) sequence (lower line, AA 1-417) of an anti-body-cytokine
      AMAIZe fusion protein
<220> FEATURE:
<221> NAME/KEY: CDS
<222> LOCATION: (1)..(1254)
<220> FEATURE:
<223> OTHER INFORMATION: Sequence of leader peptide: NT 1-57, AA 1-19
<220> FEATURE:
<223> OTHER INFORMATION: Sequence of the single chain (scFv) antibody
      fragment 40 specific for the tumor stroma antigen FAP: NT 58-801,
      AA 20-267
<220> FEATURE:
<223> OTHER INFORMATION: Sequence of the linker between scFv and the
      FasL fragment (AA 139-281): NT 802-822, AA 268-274
<220> FEATURE:
<223> OTHER INFORMATION: Sequence of the human FasL fragment
      (extracellular domain, AA 139-281 of the natural human FasL
      molecule): NT 823-1251, AA 275-417
<220> FEATURE:
<223> OTHER INFORMATION: Stop codon: NT 1552-1554

<400> SEQUENCE: 7 atg gac tgg acc tgg cgc gtg ttt tgc ctg ctc gcc gtg gct cct ggg        48
Met Asp Trp Thr Trp Arg Val Phe Cys Leu Leu Ala Val Ala Pro Gly -continued

```
  1               5                  10                 15
gcc cac agc cag gta cag ctg gtg cag tct ggg gga ggc atg gta gag      96
Ala His Ser Gln Val Gln Leu Val Gln Ser Gly Gly Gly Met Val Glu
             20                 25                 30 cct ggg ggg tcc ctt aga ctc tcc tgt gca gcc tct gga ttc act ttc     144
Pro Gly Gly Ser Leu Arg Leu Ser Cys Ala Ala Ser Gly Phe Thr Phe
             35                 40                 45 agt aat gcc tgg atg agc tgg gtc cgc cag gct cca ggg aag ggg ctg     192
Ser Asn Ala Trp Met Ser Trp Val Arg Gln Ala Pro Gly Lys Gly Leu
        50                 55                 60 gag tgg gtt ggc cgt ata aaa agc aaa gct ggt ggt ggg aca gca gag     240
Glu Trp Val Gly Arg Ile Lys Ser Lys Ala Gly Gly Gly Thr Ala Glu
 65                 70                 75                 80 tac gct gca ccc gtg aaa ggc aga ttc acc atc tca aga gat gat tca     288
Tyr Ala Ala Pro Val Lys Gly Arg Phe Thr Ile Ser Arg Asp Asp Ser
                 85                 90                 95 caa aac acg ctg tat ctg caa atg aac agc ctg aaa acc gac gac aca     336
Gln Asn Thr Leu Tyr Leu Gln Met Asn Ser Leu Lys Thr Asp Asp Thr
             100                105                110 gcc gtg tat tac tgt acc aca cat gtc tac ggt gcc ccc cgg aac tgg     384
Ala Val Tyr Tyr Cys Thr Thr His Val Tyr Gly Ala Pro Arg Asn Trp
             115                120                125 ggc cag gga tcc ctg gtc acc gtc tcc tca gcc tcc acc aag ggc cca     432
Gly Gln Gly Ser Leu Val Thr Val Ser Ser Ala Ser Thr Lys Gly Pro
        130                135                140 aag ctt gaa gaa ggt gaa ttt tca gaa gca cgc gta cag tct gtg ttg     480
Lys Leu Glu Glu Gly Glu Phe Ser Glu Ala Arg Val Gln Ser Val Leu
145                150                155                160 act cag ccg ccc tca gtg tct gcg gcc cca gga cag aag gtc acc atc     528
Thr Gln Pro Pro Ser Val Ser Ala Ala Pro Gly Gln Lys Val Thr Ile
                 165                170                175 tcc tgc tct gga agc agc tcc aac att gga aat aat tat gtc tcc tgg     576
Ser Cys Ser Gly Ser Ser Ser Asn Ile Gly Asn Asn Tyr Val Ser Trp
             180                185                190 tac gtt caa ctc cca gga aca gcc ccc aaa ctc ctc att tat gac aat     624
Tyr Val Gln Leu Pro Gly Thr Ala Pro Lys Leu Leu Ile Tyr Asp Asn
             195                200                205 aat aag cga ttc tca gga gtt cct gac cga ttc tct ggc tcc aag tct     672
Asn Lys Arg Phe Ser Gly Val Pro Asp Arg Phe Ser Gly Ser Lys Ser
        210                215                220 ggc acg tca gcc acc ctg ggc atc acc ggg ctc cag act ggg gac gag     720
Gly Thr Ser Ala Thr Leu Gly Ile Thr Gly Leu Gln Thr Gly Asp Glu
225                230                235                240 gcc gat tat tac tgc gga gca tgg gat ggc agc ctg cgt gaa gcg gta     768
Ala Asp Tyr Tyr Cys Gly Ala Trp Asp Gly Ser Leu Arg Glu Ala Val
                 245                250                255 ttc ggc gga ggg acc aag gtc acc gtc cta ggt gcg gcc gca gtt gag     816
Phe Gly Gly Gly Thr Lys Val Thr Val Leu Gly Ala Ala Ala Val Glu
             260                265                270 ctc gag gaa aaa aag gag ctg agg aaa gtg gcc cat tta aca ggc aag     864
Leu Glu Glu Lys Lys Glu Leu Arg Lys Val Ala His Leu Thr Gly Lys
             275                280                285 tcc aac tca agg tcc atg cct ctg gaa tgg gaa gac acc tat gga att     912
Ser Asn Ser Arg Ser Met Pro Leu Glu Trp Glu Asp Thr Tyr Gly Ile
        290                295                300 gtc ctg ctt tct gga gtg aag tat aag aag ggt ggc ctt gtg atc aat     960
Val Leu Leu Ser Gly Val Lys Tyr Lys Lys Gly Gly Leu Val Ile Asn
305                310                315                320 gaa act ggg ctg tac ttt gta tat tcc aaa gta tac ttc cgg ggt caa    1008
Glu Thr Gly Leu Tyr Phe Val Tyr Ser Lys Val Tyr Phe Arg Gly Gln
```

```
                Glu Thr Gly Leu Tyr Phe Val Tyr Ser Lys Val Tyr Phe Arg Gly Gln
                                325                 330                 335 tct tgc aac aac ctg ccc ctg agc cac aag gtc tac atg agg aac tct          1056
Ser Cys Asn Asn Leu Pro Leu Ser His Lys Val Tyr Met Arg Asn Ser
                340                 345                 350 aag tat ccc cag gat ctg gtg atg atg gag ggg aag atg atg agc tac          1104
Lys Tyr Pro Gln Asp Leu Val Met Met Glu Gly Lys Met Met Ser Tyr
                355                 360                 365 tgc act act ggg cag atg tgg gcc cgc agc agc tac ctg ggg gca gtg          1152
Cys Thr Thr Gly Gln Met Trp Ala Arg Ser Ser Tyr Leu Gly Ala Val
        370                 375                 380 ttc aat ctt acc agt gct gat cat tta tat gtc aac gta tct gag ctc          1200
Phe Asn Leu Thr Ser Ala Asp His Leu Tyr Val Asn Val Ser Glu Leu
385                 390                 395                 400 tct ctg gtc aat ttt gag gaa tct cag acg ttt ttc ggc tta tat aag          1248
Ser Leu Val Asn Phe Glu Glu Ser Gln Thr Phe Phe Gly Leu Tyr Lys
                    405                 410                 415 ctc taa                                                                   1254
Leu <210> SEQ ID NO 8
<211> LENGTH: 417
<212> TYPE: PRT
<213> ORGANISM: Artificial Sequence
<220> FEATURE:
<223> OTHER INFORMATION: Synthetic amino acid sequence (of an anti-body-
      cytokine AMAIZe fusion protein of the invention exemplified by
      FasL-AMAIZe(40)
<220> FEATURE:
<223> OTHER INFORMATION: Stop codon: NT 1552-1554

<400> SEQUENCE: 8

Met Asp Trp Thr Trp Arg Val Phe Cys Leu Leu Ala Val Ala Pro Gly
 1               5                  10                  15

Ala His Ser Gln Val Gln Leu Val Gln Ser Gly Gly Gly Met Val Glu
                20                  25                  30

Pro Gly Gly Ser Leu Arg Leu Ser Cys Ala Ala Ser Gly Phe Thr Phe
            35                  40                  45

Ser Asn Ala Trp Met Ser Trp Val Arg Gln Ala Pro Gly Lys Gly Leu
        50                  55                  60

Glu Trp Val Gly Arg Ile Lys Ser Lys Ala Gly Gly Gly Thr Ala Glu
 65                 70                  75                  80

Tyr Ala Ala Pro Val Lys Gly Arg Phe Thr Ile Ser Arg Asp Asp Ser
                85                  90                  95

Gln Asn Thr Leu Tyr Leu Gln Met Asn Ser Leu Lys Thr Asp Asp Thr
            100                 105                 110

Ala Val Tyr Tyr Cys Thr Thr His Val Tyr Gly Ala Pro Arg Asn Trp
        115                 120                 125

Gly Gln Gly Ser Leu Val Thr Val Ser Ser Ala Ser Thr Lys Gly Pro
    130                 135                 140

Lys Leu Glu Glu Gly Glu Phe Ser Glu Ala Arg Val Gln Ser Val Leu
145                 150                 155                 160

Thr Gln Pro Pro Ser Val Ser Ala Ala Pro Gly Gln Lys Val Thr Ile
                165                 170                 175

Ser Cys Ser Gly Ser Ser Ser Asn Ile Gly Asn Asn Tyr Val Ser Trp
            180                 185                 190

Tyr Val Gln Leu Pro Gly Thr Ala Pro Lys Leu Leu Ile Tyr Asp Asn
        195                 200                 205
```

```
Asn Lys Arg Phe Ser Gly Val Pro Asp Arg Phe Ser Gly Ser Lys Ser
    210                 215                 220
Gly Thr Ser Ala Thr Leu Gly Ile Thr Gly Leu Gln Thr Gly Asp Glu
225                 230                 235                 240
Ala Asp Tyr Tyr Cys Gly Ala Trp Asp Gly Ser Leu Arg Glu Ala Val
                245                 250                 255
Phe Gly Gly Gly Thr Lys Val Thr Val Leu Gly Ala Ala Ala Val Glu
            260                 265                 270
Leu Glu Glu Lys Lys Glu Leu Arg Lys Val Ala His Leu Thr Gly Lys
        275                 280                 285
Ser Asn Ser Arg Ser Met Pro Leu Glu Trp Glu Asp Thr Tyr Gly Ile
290                 295                 300
Val Leu Leu Ser Gly Val Lys Tyr Lys Lys Gly Gly Leu Val Ile Asn
305                 310                 315                 320
Glu Thr Gly Leu Tyr Phe Val Tyr Ser Lys Val Tyr Phe Arg Gly Gln
                325                 330                 335
Ser Cys Asn Asn Leu Pro Leu Ser His Lys Val Tyr Met Arg Asn Ser
            340                 345                 350
Lys Tyr Pro Gln Asp Leu Val Met Met Glu Gly Lys Met Met Ser Tyr
        355                 360                 365
Cys Thr Thr Gly Gln Met Trp Ala Arg Ser Ser Tyr Leu Gly Ala Val
370                 375                 380
Phe Asn Leu Thr Ser Ala Asp His Leu Tyr Val Asn Val Ser Glu Leu
385                 390                 395                 400
Ser Leu Val Asn Phe Glu Glu Ser Gln Thr Phe Phe Gly Leu Tyr Lys
                405                 410                 415
Leu

<210> SEQ ID NO 9
<211> LENGTH: 1299
<212> TYPE: DNA
<213> ORGANISM: Artificial Sequence
<220> FEATURE:
<223> OTHER INFORMATION: Synthetic coding DNA sequence (upper line,
      coding DNA strand, nucleotide (NT) 1-1299) and translated amino
      acid (AA) sequence (lower line, AA 1-432) of an anti-body-cytokine
      AMAIZe fusion protein
<220> FEATURE:
<221> NAME/KEY: CDS
<222> LOCATION: (1)..(1299)
<220> FEATURE:
<223> OTHER INFORMATION: Sequence of leader peptide: NT 1-57, AA 1-19
<220> FEATURE:
<223> OTHER INFORMATION: Sequence of the single chain (scFv) antibody
      fragment OS4 specific for the tumor stroma antigen FAP: NT 58-822,
      AA 20-274
<220> FEATURE:
<223> OTHER INFORMATION: Sequence of the linker between scFv and the
      FasL fragment (AA 139-281): NT 823-867, AA 275-289
<220> FEATURE:
<223> OTHER INFORMATION: Sequence of the human FasL fragment
      (extracellular domain, AA 139-281 of the natural human FasL
      molecule): NT 868-1296, AA 290-432
<220> FEATURE:
<223> OTHER INFORMATION: Stop codon: NT 1441-1443

<400> SEQUENCE: 9 atg gac tgg acc tgg cgc gtg ttt tgc ctg ctc gcc gtg gct cct ggg    48
Met Asp Trp Thr Trp Arg Val Phe Cys Leu Leu Ala Val Ala Pro Gly
1               5                   10                  15 gcc cac agc cag gtg caa cta gtg cag tcc ggc gcc gaa gtg aag aaa    96
Ala His Ser Gln Val Gln Leu Val Gln Ser Gly Ala Glu Val Lys Lys
            20                  25                  30
```

```
ccc ggt gct tcc gtg aaa gtc agc tgt aaa act agt aga tac acc ttc    144
Pro Gly Ala Ser Val Lys Val Ser Cys Lys Thr Ser Arg Tyr Thr Phe
             35                  40                  45 act gaa tac acc ata cac tgg gtt aga cag gcc cct ggc caa agg ctg    192
Thr Glu Tyr Thr Ile His Trp Val Arg Gln Ala Pro Gly Gln Arg Leu
 50                  55                  60 gag tgg ata gga ggt att aat cct aac aat ggt att cct aac tac aac    240
Glu Trp Ile Gly Gly Ile Asn Pro Asn Asn Gly Ile Pro Asn Tyr Asn
 65                  70                  75                  80 cag aag ttc aag ggc cgg gtc acc atc acc gta gac acc tct gcc agc    288
Gln Lys Phe Lys Gly Arg Val Thr Ile Thr Val Asp Thr Ser Ala Ser
                 85                  90                  95 acc gcc tac atg gaa ctg tcc agc ctg cgc tcc gag gac act gca gtc    336
Thr Ala Tyr Met Glu Leu Ser Ser Leu Arg Ser Glu Asp Thr Ala Val
                100                 105                 110 tac tac tgc gcc aga aga aga atc gcc tat ggt tac gac gag ggc cat    384
Tyr Tyr Cys Ala Arg Arg Arg Ile Ala Tyr Gly Tyr Asp Glu Gly His
            115                 120                 125 gct atg gac tac tgg ggt caa gga acc ctt gtc acc gtc tcc tca gcc    432
Ala Met Asp Tyr Trp Gly Gln Gly Thr Leu Val Thr Val Ser Ser Ala
130                 135                 140 tcc acc aag ggc cca aag ctt gaa gaa ggt gaa ttt tca gaa gca cgc    480
Ser Thr Lys Gly Pro Lys Leu Glu Glu Gly Glu Phe Ser Glu Ala Arg
145                 150                 155                 160 gta gac att gtg atg acc caa tct cca gac tct ttg gct gtg tct cta    528
Val Asp Ile Val Met Thr Gln Ser Pro Asp Ser Leu Ala Val Ser Leu
                165                 170                 175 ggg gag agg gcc acc atc aac tgc aag tcc agt cag agc ctt tta tat    576
Gly Glu Arg Ala Thr Ile Asn Cys Lys Ser Ser Gln Ser Leu Leu Tyr
            180                 185                 190 tct aga aat caa aag aac tac ttg gcc tgg tat cag cag aaa cca gga    624
Ser Arg Asn Gln Lys Asn Tyr Leu Ala Trp Tyr Gln Gln Lys Pro Gly
        195                 200                 205 cag cca ccc aaa ctc ctc atc ttt tgg gct agc act agg gaa tct ggg    672
Gln Pro Pro Lys Leu Leu Ile Phe Trp Ala Ser Thr Arg Glu Ser Gly
210                 215                 220 gta cct gat agg ttc agt ggc agt ggg ttt ggg aca gac ttc acc ctc    720
Val Pro Asp Arg Phe Ser Gly Ser Gly Phe Gly Thr Asp Phe Thr Leu
225                 230                 235                 240 acc att agc agc ctg cag gct gaa gat gtg gca gtt tat tac tgt cag    768
Thr Ile Ser Ser Leu Gln Ala Glu Asp Val Ala Val Tyr Tyr Cys Gln
                245                 250                 255 caa tat ttt agc tat ccg ctc acg ttc gga caa ggg acc aag gtg gaa    816
Gln Tyr Phe Ser Tyr Pro Leu Thr Phe Gly Gln Gly Thr Lys Val Glu
            260                 265                 270 ata aaa cgt act gtg gct gca cca tct gtc ttc gct gtc ttc gcg gcc    864
Ile Lys Arg Thr Val Ala Ala Pro Ser Val Phe Ala Val Phe Ala Ala
        275                 280                 285 gca gaa aaa aag gag ctg agg aaa gtg gcc cat tta aca ggc aag tcc    912
Ala Glu Lys Lys Glu Leu Arg Lys Val Ala His Leu Thr Gly Lys Ser
290                 295                 300 aac tca agg tcc atg cct ctg gaa tgg gaa gac acc tat gga att gtc    960
Asn Ser Arg Ser Met Pro Leu Glu Trp Glu Asp Thr Tyr Gly Ile Val
305                 310                 315                 320 ctg ctt tct gga gtg aag tat aag aag ggt ggc ctt gtg atc aat gaa   1008
Leu Leu Ser Gly Val Lys Tyr Lys Lys Gly Gly Leu Val Ile Asn Glu
                325                 330                 335 act ggg ctg tac ttt gta tat tcc aaa gta tac ttc cgg ggt caa tct   1056
Thr Gly Leu Tyr Phe Val Tyr Ser Lys Val Tyr Phe Arg Gly Gln Ser
```

```
                   340              345              350
tgc aac aac ctg ccc ctg agc cac aag gtc tac atg agg aac tct aag    1104
Cys Asn Asn Leu Pro Leu Ser His Lys Val Tyr Met Arg Asn Ser Lys
            355              360              365 tat ccc cag gat ctg gtg atg atg gag ggg aag atg atg agc tac tgc    1152
Tyr Pro Gln Asp Leu Val Met Met Glu Gly Lys Met Met Ser Tyr Cys
370              375              380 act act ggg cag atg tgg gcc cgc agc agc tac ctg ggg gca gtg ttc    1200
Thr Thr Gly Gln Met Trp Ala Arg Ser Ser Tyr Leu Gly Ala Val Phe
385              390              395              400 aat ctt acc agt gct gat cat tta tat gtc aac gta tct gag ctc tct    1248
Asn Leu Thr Ser Ala Asp His Leu Tyr Val Asn Val Ser Glu Leu Ser
            405              410              415 ctg gtc aat ttt gag gaa tct cag acg ttt ttc ggc tta tat aag ctc    1296
Leu Val Asn Phe Glu Glu Ser Gln Thr Phe Phe Gly Leu Tyr Lys Leu
        420              425              430 taa                                                                1299

<210> SEQ ID NO 10
<211> LENGTH: 432
<212> TYPE: PRT
<213> ORGANISM: Artificial Sequence
<220> FEATURE:
<223> OTHER INFORMATION: Synthetic amino acid sequence of an anti-body-
      cytokine AMAIZe fusion protein of the invention exemplified by
      FasL-AMAIZe(OS4)
<220> FEATURE:
<223> OTHER INFORMATION: Stop codon: NT 1441-1443

<400> SEQUENCE: 10

Met Asp Trp Thr Trp Arg Val Phe Cys Leu Leu Ala Val Ala Pro Gly
 1               5                  10                  15

Ala His Ser Gln Val Gln Leu Val Gln Ser Gly Ala Glu Val Lys Lys
            20                  25                  30

Pro Gly Ala Ser Val Lys Val Ser Cys Lys Thr Ser Arg Tyr Thr Phe
        35                  40                  45

Thr Glu Tyr Thr Ile His Trp Val Arg Gln Ala Pro Gly Gln Arg Leu
    50                  55                  60

Glu Trp Ile Gly Gly Ile Asn Pro Asn Asn Gly Ile Pro Asn Tyr Asn
65                  70                  75                  80

Gln Lys Phe Lys Gly Arg Val Thr Ile Thr Val Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Arg Ile Ala Tyr Gly Tyr Asp Glu Gly His
        115                 120                 125

Ala Met Asp Tyr Trp Gly Gln Gly Thr Leu Val Thr Val Ser Ser Ala
    130                 135                 140

Ser Thr Lys Gly Pro Lys Leu Glu Glu Gly Glu Phe Ser Glu Ala Arg
145                 150                 155                 160

Val Asp Ile Val Met Thr Gln Ser Pro Asp Ser Leu Ala Val Ser Leu
                165                 170                 175

Gly Glu Arg Ala Thr Ile Asn Cys Lys Ser Ser Gln Ser Leu Leu Tyr
            180                 185                 190

Ser Arg Asn Gln Lys Asn Tyr Leu Ala Trp Tyr Gln Gln Lys Pro Gly
        195                 200                 205

Gln Pro Pro Lys Leu Leu Ile Phe Trp Ala Ser Thr Arg Glu Ser Gly
    210                 215                 220
```

```
Val Pro Asp Arg Phe Ser Gly Ser Gly Phe Gly Thr Asp Phe Thr Leu
225                 230                 235                 240

Thr Ile Ser Ser Leu Gln Ala Glu Asp Val Ala Val Tyr Tyr Cys Gln
                245                 250                 255

Gln Tyr Phe Ser Tyr Pro Leu Thr Phe Gly Gln Gly Thr Lys Val Glu
            260                 265                 270

Ile Lys Arg Thr Val Ala Ala Pro Ser Val Phe Ala Val Phe Ala Ala
        275                 280                 285

Ala Glu Lys Lys Glu Leu Arg Lys Val Ala His Leu Thr Gly Lys Ser
    290                 295                 300

Asn Ser Arg Ser Met Pro Leu Glu Trp Glu Asp Thr Tyr Gly Ile Val
305                 310                 315                 320

Leu Leu Ser Gly Val Lys Tyr Lys Lys Gly Gly Leu Val Ile Asn Glu
                325                 330                 335

Thr Gly Leu Tyr Phe Val Tyr Ser Lys Val Tyr Phe Arg Gly Gln Ser
            340                 345                 350

Cys Asn Asn Leu Pro Leu Ser His Lys Val Tyr Met Arg Asn Ser Lys
        355                 360                 365

Tyr Pro Gln Asp Leu Val Met Met Glu Gly Lys Met Met Ser Tyr Cys
    370                 375                 380

Thr Thr Gly Gln Met Trp Ala Arg Ser Ser Tyr Leu Gly Ala Val Phe
385                 390                 395                 400

Asn Leu Thr Ser Ala Asp His Leu Tyr Val Asn Val Ser Glu Leu Ser
                405                 410                 415

Leu Val Asn Phe Glu Glu Ser Gln Thr Phe Phe Gly Leu Tyr Lys Leu
            420                 425                 430

<210> SEQ ID NO 11
<211> LENGTH: 1278
<212> TYPE: DNA
<213> ORGANISM: Artificial Sequence
<220> FEATURE:
<223> OTHER INFORMATION: Synthetic coding DNA sequence (upper line,
      coding DNA strand, nucleotide (NT) 1-1278) and translated amino
      acid (AA) sequence (lower line, AA 1-425) of an anti-body-cytokine
      AMAIZe fusion protein
<220> FEATURE:
<221> NAME/KEY: CDS
<222> LOCATION: (1)..(1278)
<220> FEATURE:
<223> OTHER INFORMATION: Sequence of leader peptide: NT 1-57, AA 1-19
<220> FEATURE:
<223> OTHER INFORMATION: Sequence of the single chain (scFv) antibody
      fragment 40 specific for the tumor stroma antigen FAP: NT 58-801,
      AA 20-267
<220> FEATURE:
<223> OTHER INFORMATION: Sequence of the Flag-tag between scFv and the
      linker sequence: NT 802-825, AA 268-275
<220> FEATURE:
<223> OTHER INFORMATION: Sequence of the linker between the Flag-tag and
      the FasL fragment (AA 139-281): NT 826-846, AA 276-282
<220> FEATURE:
<223> OTHER INFORMATION: Sequence of the human FasL fragment
      (extracellular domain, AA 139-281 of the natural human FasL
      molecule): NT 847-1275, AA 283-425
<220> FEATURE:
<223> OTHER INFORMATION: Stop codon: NT 1276-1278

<400> SEQUENCE: 11 atg gac tgg acc tgg cgc gtg ttt tgc ctg ctc gcc gtg gct cct ggg    48
Met Asp Trp Thr Trp Arg Val Phe Cys Leu Leu Ala Val Ala Pro Gly
  1               5                  10                  15 gcc cac agc cag gta cag ctg gtg cag tct ggg gga ggc atg gta gag    96
```

```
                Ala His Ser Gln Val Gln Leu Val Gln Ser Gly Gly Gly Met Val Glu
                         20                  25                  30 cct ggg ggg tcc ctt aga ctc tcc tgt gca gcc tct gga ttc act ttc      144
Pro Gly Gly Ser Leu Arg Leu Ser Cys Ala Ala Ser Gly Phe Thr Phe
             35                  40                  45 agt aat gcc tgg atg agc tgg gtc cgc cag gct cca ggg aag ggg ctg      192
Ser Asn Ala Trp Met Ser Trp Val Arg Gln Ala Pro Gly Lys Gly Leu
 50                  55                  60 gag tgg gtt ggc cgt ata aaa agc aaa gct ggt ggt ggg aca gca gag      240
Glu Trp Val Gly Arg Ile Lys Ser Lys Ala Gly Gly Gly Thr Ala Glu
 65                  70                  75                  80 tac gct gca ccc gtg aaa ggc aga ttc acc atc tca aga gat gat tca      288
Tyr Ala Ala Pro Val Lys Gly Arg Phe Thr Ile Ser Arg Asp Asp Ser
                 85                  90                  95 caa aac acg ctg tat ctg caa atg aac agc ctg aaa acc gac gac aca      336
Gln Asn Thr Leu Tyr Leu Gln Met Asn Ser Leu Lys Thr Asp Asp Thr
            100                 105                 110 gcc gtg tat tac tgt acc aca cat gtc tac ggt gcc ccc cgg aac tgg      384
Ala Val Tyr Tyr Cys Thr Thr His Val Tyr Gly Ala Pro Arg Asn Trp
        115                 120                 125 ggc cag gga tcc ctg gtc acc gtc tcc tca gcc tcc acc aag ggc cca      432
Gly Gln Gly Ser Leu Val Thr Val Ser Ser Ala Ser Thr Lys Gly Pro
    130                 135                 140 aag ctt gaa gaa ggt gaa ttt tca gaa gca cgc gta cag tct gtg ttg      480
Lys Leu Glu Glu Gly Glu Phe Ser Glu Ala Arg Val Gln Ser Val Leu
145                 150                 155                 160 act cag ccg ccc tca gtg tct gcg gcc cca gga cag aag gtc acc atc      528
Thr Gln Pro Pro Ser Val Ser Ala Ala Pro Gly Gln Lys Val Thr Ile
                165                 170                 175 tcc tgc tct gga agc agc tcc aac att gga aat aat tat gtc tcc tgg      576
Ser Cys Ser Gly Ser Ser Ser Asn Ile Gly Asn Asn Tyr Val Ser Trp
            180                 185                 190 tac gtt caa ctc cca gga aca gcc ccc aaa ctc ctc att tat gac aat      624
Tyr Val Gln Leu Pro Gly Thr Ala Pro Lys Leu Leu Ile Tyr Asp Asn
        195                 200                 205 aat aag cga ttc tca gga gtt cct gac cga ttc tct ggc tcc aag tct      672
Asn Lys Arg Phe Ser Gly Val Pro Asp Arg Phe Ser Gly Ser Lys Ser
    210                 215                 220 ggc acg tca gcc acc ctg ggc atc acc ggg ctc cag act ggg gac gag      720
Gly Thr Ser Ala Thr Leu Gly Ile Thr Gly Leu Gln Thr Gly Asp Glu
225                 230                 235                 240 gcc gat tat tac tgc gga gca tgg gat ggc agc ctg cgt gaa gcg gta      768
Ala Asp Tyr Tyr Cys Gly Ala Trp Asp Gly Ser Leu Arg Glu Ala Val
                245                 250                 255 ttc ggc gga ggg acc aag gtc acc gtc cta ggt gat tac aaa gac gat      816
Phe Gly Gly Gly Thr Lys Val Thr Val Leu Gly Asp Tyr Lys Asp Asp
            260                 265                 270 gac gat aaa gcg gcc gca gtt gag ctc gag gaa aaa aag gag ctg agg      864
Asp Asp Lys Ala Ala Ala Val Glu Leu Glu Glu Lys Lys Glu Leu Arg
        275                 280                 285 aaa gtg gcc cat tta aca ggc aag tcc aac tca agg tcc atg cct ctg      912
Lys Val Ala His Leu Thr Gly Lys Ser Asn Ser Arg Ser Met Pro Leu
    290                 295                 300 gaa tgg gaa gac acc tat gga att gtc ctg ctt tct gga gtg aag tat      960
Glu Trp Glu Asp Thr Tyr Gly Ile Val Leu Leu Ser Gly Val Lys Tyr
305                 310                 315                 320 aag aag ggt ggc ctt gtg atc aat gaa act ggg ctg tac ttt gta tat     1008
Lys Lys Gly Gly Leu Val Ile Asn Glu Thr Gly Leu Tyr Phe Val Tyr
                325                 330                 335
```

```
tcc aaa gta tac ttc cgg ggt caa tct tgc aac aac ctg ccc ctg agc    1056
Ser Lys Val Tyr Phe Arg Gly Gln Ser Cys Asn Asn Leu Pro Leu Ser
        340                 345                 350 cac aag gtc tac atg agg aac tct aag tat ccc cag gat ctg gtg atg    1104
His Lys Val Tyr Met Arg Asn Ser Lys Tyr Pro Gln Asp Leu Val Met
        355                 360                 365 atg gag ggg aag atg atg agc tac tgc act act ggg cag atg tgg gcc    1152
Met Glu Gly Lys Met Met Ser Tyr Cys Thr Thr Gly Gln Met Trp Ala
370                 375                 380 cgc agc agc tac ctg ggg gca gtg ttc aat ctt acc agt gct gat cat    1200
Arg Ser Ser Tyr Leu Gly Ala Val Phe Asn Leu Thr Ser Ala Asp His
385                 390                 395                 400 tta tat gtc aac gta tct gag ctc tct ctg gtc aat ttt gag gaa tct    1248
Leu Tyr Val Asn Val Ser Glu Leu Ser Leu Val Asn Phe Glu Glu Ser
                405                 410                 415 cag acg ttt ttc ggc tta tat aag ctc taa                            1278
Gln Thr Phe Phe Gly Leu Tyr Lys Leu
                420                 425

<210> SEQ ID NO 12
<211> LENGTH: 425
<212> TYPE: PRT
<213> ORGANISM: Artificial Sequence
<220> FEATURE:
<223> OTHER INFORMATION: Synthetic amino acid sequence of an anti-body-
      cytokine AMAIZe fusion protein of the invention exemplified by
      FasL-AMAIZe (40-Flag)
<220> FEATURE:
<223> OTHER INFORMATION: Stop codon: NT 1276

```
Gly Thr Ser Ala Thr Leu Gly Ile Thr Gly Leu Gln Thr Gly Asp Glu
225                 230                 235                 240

Ala Asp Tyr Tyr Cys Gly Ala Trp Asp Gly Ser Leu Arg Glu Ala Val
            245                 250                 255

Phe Gly Gly Gly Thr Lys Val Thr Val Leu Gly Asp Tyr Lys Asp Asp
        260                 265                 270

Asp Asp Lys Ala Ala Val Glu Leu Glu Lys Lys Glu Leu Arg
    275                 280                 285

Lys Val Ala His Leu Thr Gly Lys Ser Asn Ser Arg Ser Met Pro Leu
290                 295                 300

Glu Trp Glu Asp Thr Tyr Gly Ile Val Leu Leu Ser Gly Val Lys Tyr
305                 310                 315                 320

Lys Lys Gly Gly Leu Val Ile Asn Glu Thr Gly Leu Tyr Phe Val Tyr
                325                 330                 335

Ser Lys Val Tyr Phe Arg Gly Gln Ser Cys Asn Asn Leu Pro Leu Ser
            340                 345                 350

His Lys Val Tyr Met Arg Asn Ser Lys Tyr Pro Gln Asp Leu Val Met
        355                 360                 365

Met Glu Gly Lys Met Met Ser Tyr Cys Thr Thr Gly Gln Met Trp Ala
370                 375                 380

Arg Ser Ser Tyr Leu Gly Ala Val Phe Asn Leu Thr Ser Ala Asp His
385                 390                 395                 400

Leu Tyr Val Asn Val Ser Glu Leu Ser Leu Val Asn Phe Glu Glu Ser
                405                 410                 415

Gln Thr Phe Phe Gly Leu Tyr Lys Leu
            420                 425

<210> SEQ ID NO 13
<211> LENGTH: 187
<212> TYPE: PRT
<213> ORGANISM: Homo sapiens

<400> SEQUENCE: 13

Thr Ser Glu Glu Thr Ile Ser Thr Val Gln Glu Lys Gln Gln Asn Ile
1               5                   10                  15

Ser Pro Leu Val Arg Glu Arg Gly Pro Gln Arg Val Ala Ala His Ile
            20                  25                  30

Thr Gly Thr Arg Gly Arg Ser Asn Thr Leu Ser Ser Pro Asn Ser Lys
        35                  40                  45

Asn Glu Lys Ala Leu Gly Arg Lys Ile Asn Ser Trp Glu Ser Ser Arg
    50                  55                  60

Ser Gly His Ser Phe Leu Ser Asn Leu His Leu Arg Asn Gly Glu Leu
65                  70                  75                  80

Val Ile His Glu Lys Gly Phe Tyr Tyr Ile Tyr Ser Gln Thr Tyr Phe
                85                  90                  95

Arg Phe Gln Glu Glu Ile Lys Glu Asn Thr Lys Asn Asp Lys Gln Met
            100                 105                 110

Val Gln Tyr Ile Tyr Lys Tyr Thr Ser Tyr Pro Asp Pro Ile Leu Leu
        115                 120                 125

Met Lys Ser Ala Arg Asn Ser Cys Trp Ser Lys Asp Ala Glu Tyr Gly
130                 135                 140

Leu Tyr Ser Ile Tyr Gln Gly Gly Ile Phe Glu Leu Lys Glu Asn Asp
145                 150                 155                 160

Arg Ile Phe Val Ser Val Thr Asn Glu His Leu Ile Asp Met Asp His
```

165                 170                 175

Glu Ala Ser Phe Phe Gly Ala Phe Leu Val Gly
            180                 185

<210> SEQ ID NO 14
<211> LENGTH: 143
<212> TYPE: PRT
<213> ORGANISM: Homo sapiens

<400> SEQUENCE: 14

Glu Lys Lys Glu Leu Arg Lys Val Ala His Leu Thr Gly Lys Ser Asn
 1               5                  10                  15

Ser Arg Ser Met Pro Leu Glu Trp Glu Asp Thr Tyr Gly Ile Val Leu
            20                  25                  30

Leu Ser Gly Val Lys Tyr Lys Gly Gly Leu Val Ile Asn Glu Thr
        35                  40                  45

Gly Leu Tyr Phe Val Tyr Ser Lys Val Tyr Phe Arg Gly Gln Ser Cys
    50                  55                  60

Asn Asn Leu Pro Leu Ser His Lys Val Tyr Met Arg Asn Ser Lys Tyr
65                  70                  75                  80

Pro Gln Asp Leu Val Met Met Glu Gly Lys Met Met Ser Tyr Cys Thr
                85                  90                  95

Thr Gly Gln Met Trp Ala Arg Ser Ser Tyr Leu Gly Ala Val Phe Asn
            100                 105                 110

Leu Thr Ser Ala Asp His Leu Tyr Val Asn Val Ser Glu Leu Ser Leu
        115                 120                 125

Val Asn Phe Glu Glu Ser Gln Thr Phe Phe Gly Leu Tyr Lys Leu
    130                 135                 140

<210> SEQ ID NO 15
<211> LENGTH: 104
<212> TYPE: PRT
<213> ORGANISM: Artificial Sequence
<220> FEATURE:
<223> OTHER INFORMATION: A snythetic peptide

<400> SEQUENCE: 15

Gly Gln Pro Arg Glu Pro Gln Val Tyr Thr Leu Pro Pro Ser Arg Glu
 1               5                  10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser
            100

<210> SEQ ID NO 16
<211> LENGTH: 109
<212> TYPE: PRT
<213> ORGANISM: Gallus gallus

<400> SEQUENCE: 16

```
Gln Lys Arg Glu Thr Gly Leu Asn Val Thr Leu Pro Glu Asp Asn Gln
  1               5                  10                  15

Pro Val Val Phe Asn His Val Tyr Asn Ile Lys Leu Pro Val Gly Ser
             20                  25                  30

Leu Cys Ser Val Asp Leu Asp Thr Ala Ser Gly Asp Ala Asp Leu Lys
         35                  40                  45

Ala Glu Ile Glu Pro Val Lys Asn Tyr Glu Glu His Thr Val Asn Glu
     50                  55                  60

Gly Asn Gln Ile Val Phe Thr His Arg Ile Asn Ile Pro Arg Arg Ala
 65                  70                  75                  80

Cys Gly Cys Ala Ala Ala Pro Asp Ile Lys Asp Leu Leu Ser Arg Leu
             85                  90                  95

Glu Glu Leu Glu Gly Leu Val Ser Ser Leu Arg Glu Gln
            100                 105
```

<210> SEQ ID NO 17
<211> LENGTH: 109
<212> TYPE: PRT
<213> ORGANISM: Homo sapiens

<400> SEQUENCE: 17

```
His Lys Arg Gln Ser Gly Val Asn Ala Thr Leu Pro Glu Glu Asn Gln
  1               5                  10                  15

Pro Val Val Phe Asn His Val Tyr Asn Ile Lys Leu Pro Val Gly Ser
             20                  25                  30

Gln Cys Ser Val Asp Leu Glu Ser Ala Ser Gly Glu Lys Asp Leu Ala
         35                  40                  45

Pro Pro Ser Glu Pro Ser Glu Ser Phe Gln Glu His Thr Val Asp Gly
     50                  55                  60

Glu Asn Gln Ile Val Phe Thr His Arg Ile Asn Ile Pro Arg Arg Ala
 65                  70                  75                  80

Cys Gly Cys Ala Ala Ala Pro Asp Val Lys Glu Leu Leu Ser Arg Leu
             85                  90                  95

Glu Glu Leu Glu Asn Leu Val Ser Ser Leu Arg Glu Gln
            100                 105
```

<210> SEQ ID NO 18
<211> LENGTH: 40
<212> TYPE: PRT
<213> ORGANISM: Artificial Sequence
<220> FEATURE:
<223> OTHER INFORMATION: A synthetic polypeptide

<400> SEQUENCE: 18

```
Arg Thr Val Ala Ala Pro Ser Val Phe Ala Val Phe Ala Ala Ala Val
  1               5                  10                  15

Glu Pro Lys Ser Cys Asp Lys Thr His Thr Cys Pro Pro Cys Gly Gly
             20                  25                  30

Gly Ser Gly Gly Gly Ser Gly
         35                  40
```

<210> SEQ ID NO 19
<211> LENGTH: 9
<212> TYPE: PRT
<213> ORGANISM: Artificial Sequence
<220> FEATURE:
<223> OTHER INFORMATION: A synthetic polypeptide

<400> SEQUENCE: 19

```
Gly Gly Gly Gly Thr Gly Gly Gly Ser
  1               5

<210> SEQ ID NO 20
<211> LENGTH: 19
<212> TYPE: PRT
<213> ORGANISM: Artificial Sequence
<220> FEATURE:
<223> OTHER INFORMATION: A synthetic polypeptide

<400> SEQUENCE: 20

Arg Thr Val Ala Ala Pro Ser Val Phe Ala Val Phe Ala Ala Ala Val
  1               5                   10                  15

Glu Leu Glu

<210> SEQ ID NO 21
<211> LENGTH: 7
<212> TYPE: PRT
<213> ORGANISM: Artificial Sequence
<220> FEATURE:
<223> OTHER INFORMATION: A synthetic polypeptide

<400> SEQUENCE: 21

Ala Ala Ala Val Glu Leu Glu
  1               5

<210> SEQ ID NO 22
<211> LENGTH: 15
<212> TYPE: PRT
<213> ORGANISM: Artificial Sequence
<220> FEATURE:
<223> OTHER INFORMATION: A synthetic polypeptide

<400> SEQUENCE: 22

Arg Thr Val Ala Ala Pro Ser Val Phe Ala Val Phe Ala Ala Ala
  1               5                   10                  15

<210> SEQ ID NO 23
<211> LENGTH: 8
<212> TYPE: PRT
<213> ORGANISM: Artificial Sequence
<220> FEATURE:
<223> OTHER INFORMATION: A synthetic polypeptide

<400> SEQUENCE: 23

Asp Tyr Lys Asp Asp Asp Asp Lys
  1               5

<210> SEQ ID NO 24
<211> LENGTH: 36
<212> TYPE: DNA
<213> ORGANISM: Artificial Sequence
<220> FEATURE:
<223> OTHER INFORMATION: A synthetic oligonucleotide

<400> SEQUENCE: 24
cggggtacct cgaccatgga gtggacctgg cgcgtg                            36

<210> SEQ ID NO 25
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 25
```

```
<210> SEQ ID NO 26
<211> LENGTH: 51
<212> TYPE: DNA
<213> ORGANISM: Artificial Sequence
<220> FEATURE:
<223> OTHER INFORMATION: A synthetic oligonucleotide

<400> SEQUENCE: 26
ctaggtgcgg ccgcagttga gctcgaggaa aaaaggagc tgaggaaagt g            51

<210> SEQ ID NO 27
<211> LENGTH: 36
<212> TYPE: DNA
<213> ORGANISM: Artificial Sequence
<220> FEATURE:
<223> OTHER INFORMATION: A synthetic oligonucleotide

<400> SEQUENCE: 27
ctagctagcg tgcttctctt agagcttata taagcc                            36

<210> SEQ ID NO 28
<211> LENGTH: 52
<212> TYPE: DNA
<213> ORGANISM: Artificial Sequence
<220> FEATURE:
<223> OTHER INFORMATION: A synthetic oligonucleotide

<400> SEQUENCE: 28
gtcttcgcgg ccgcagttga gctcgagacc tctgaggaaa ccatttctac ag          52

<210> SEQ ID NO 29
<211> LENGTH: 36
<212> TYPE: DNA
<213> ORGANISM: Artificial Sequence
<220> FEATURE:
<223> OTHER INFORMATION: A synthetic oligonucleotide

<400> SEQUENCE: 29
tgctctagac caggtcagtt agccaactaa aaaggc                            36
```

SITE-SPECIFIC ANTIBODY-MEDIATED ACTIVATION OF PROAPOPTOTIC CYTOKINES: AMAIZEE (ANTIBODY-MEDIATED APOPTOSIS INDUCING CYTOKINES)

This application is a continuation under 35 U.S.C. 111(a) of PCT/EP01/10364 filed on Sep. 7, 2001 and published in English as WO 02/022680 A3 on Mar. 21, 2002, which claims priority from German application 100 45 591.3 filed on Sep. 15, 2000, which applications and publication are incorporated herein by reference.

The present invention relates to polypeptides which have as such no or a limited biological activity and which are only active when correspondingly activated by site-specific and antibody-mediated binding, the polypeptides containing a region being a peptide linker, further containing an antibody region or a region derived from an antibody, said region selectively recognizing a specific molecule on a cell surface, and further containing a cytokine moiety which has on its own no or only a limited biological activity. Furthermore, the present invention relates to nucleic acid sequences the polypeptides are based upon, vectors containing these nucleic acid sequences according to the present invention, cells transfected with nucleic acid sequences or vectors according to the present invention, uses of the subject matter of the present invention for therapeutic purposes, and compositions containing the subject matter of the present application.

Cytokines, e.g. members of the family of TNF-ligands, e.g. TRAIL (TNF Related Apoptose Inducing Ligand), also called Apo2L (Wiley et al. (1995), Immunity 6: 673-682, Pitti et al. (1996) J. Biol. Chem. 271: 12687-12689), and e.g. FasL, show a strong apoptotic activity on many tumor cells of animal and human origin in in vitro studies. In the case of TRAIL it appears that non-malignant cells are not affected. Moreover, in the preclinic animal model studies (mouse, monkey), no clues were found for an acute toxicity or other systemic side effects of TRAIL which could be seen as therapy limiting (Walczak et al. (1999) Nat. Med. 5: 157-163; Ashkenazi et al. (1999) J. Clin. Invest. 104: 155-162). Recent in vitro studies on human primary hepatocytes, however, showed a strong cytotoxic activity, e.g. in the case of a recombinantly produced TRAIL product and of a membrane-bound TRAIL of the naturally occurring form of this cytokine, respectively (Jo et al. (2000) Nat. Med. 6: 564-567; Ichikawa et al. (2001) Nat. Med. 7: 954-960). Therefore, a direct clinical application of the hitherto available cytokines, e.g. recombinant TRAIL molecules which completely mimic the reactivity of the membrane-bound TRAIL, is precluded. Furthermore, also for the related molecule FasL (ligand of the FasL receptor (Fas, CD95), the prototype of apoptotic cytokines, a clinical application was a priori excluded for safety reasons, since agonistic antibodies against its receptor, Fas, are extremely hepatotoxic in vivo (Ogasawara et al. (1993) Nature 364: 806-809). Finally, it was also shown that FasL in its soluble form displays virtually no bioactivity, in contrast to its membrane-bound form (Schneider et al. (1998) J. Exp. Med. 187: 1205-1213).

Consequently, the members of the family of TNF-ligands being available in the prior art are not applicable or can only be applied in a limited manner (e.g. in the case of TNF under so-called "isolated limb perfusion" conditions) for therapeutic applications, e.g. in the treatment of tumours, either due to a lack of bioactivity or due to extreme toxicity.

Therefore, the problem underlying the present invention is to exert the cytokine activity in a directed and tissue or cell specific way and, consequently, to avoid or at least to strictly limit undesirable potentially systemic side effects in clinical applications on tissues/cells which do not belong to the target tissue.

This problem is solved by the subject matter of the present application. At this, the present invention is based on the fact that naturally membrane-bound occurring cytokines have either no or only a limited biological activity, e.g. on certain membrane receptor subtypes, when they are proteolytically processed by the organism into a soluble form corresponding to the extracellular domain. This applies also to recombinantly produced derivates corresponding to the extracellular domain of the respective ligand. It is the finding of the present invention that such a cytokine having no activity/a limited activity regains its (full) biological activity, namely with respect to the target cells themselves as well as with respect to neighbouring cells, provided that these cells express the respective corresponding cytokine receptors for the antibody-cytokine fusion protein used, by e.g. antibody-mediated specific binding to a cell membrane-bound antigen.

Accordingly, in a first embodiment the present invention provides polypeptides containing (i) a segment (1) having a biological activity for a specific target molecule, (ii) N-terminally of segment (1) a segment (2) which is a peptide linker, and (iii) a segment (3) selectively recognising a further specific target molecule on a cell surface. At this, segment (3) is located at the N-terminus of a polypeptide according to the present invention, segment (2) following C-terminally at first, and segment (3) is located further C-terminally. Such polypeptides of the present invention (=fusion proteins according to the present invention, =constructs according the present invention) are biologically inactive/have a limited activity without site-specific and/or selective binding of segment (3) to the target molecule.

According to a preferred embodiment the polypeptides of the present invention contain in their segment (1) an amino acid sequence of a cytokine, a functional variant of a cytokine sequence or a fragment thereof. A functional variant means sequences which comprise at least a part, preferably at least 50%, more preferred at least 80%, of the native sequence, and which differ from the native sequence, e.g. by deletion(s), insertion(s) and/or at least one mutation. With respect to their spectrum of activity or their functionality, the functional variants in the sense of this invention are largely or almost congruent to the native embodiments. At this, a sequence homology of at least 90, preferably at least 95 and most preferred at least 97% to the corresponding native sequence is preferred. A functional fragment can be N-terminally, C-terminally or intrasequentially shortened native cytokine sequences, in particular certain domains, preferably at least one, more preferably an extracellular domain of the native full-length sequence. Also, biologically active variants of these fragments are disclosed according to the present invention.

In this context, such cytokines, functional variants or fragments thereof are preferred, which are members of the TNF-family.

Further preferred are such polypeptides of the present invention which contain as segment (1) an extracellular domain (or the extracellular sequence region) of a cytokine, a functional variant of an extracellular domain (or of the extracellular sequence region) or a functional fragment of an extracellular domain (or the extracellular sequence region), in particular if the cytokine is a member of the family of TNF ligands, especially the proapoptotic members thereof. Preferably, the derived variants in the sense of the present invention will have selective receptor binding properties, whereby the variant may be optimised, e.g. with respect to its specific bioactivity or other properties (stability).

Especially preferred as segment (1) is an extracellular domain, a functional variant of an extracellular domain or a functional fragment of an extracellular domain of TRAIL (TNF Related Apoptosis Inducing Ligand, AA 95-281, NCBI Accession No. AAC5032 U37518) or of FasL (AA 139-281, NCBI Accession No. AAC50124 U11821).

The mode of activity of such constructs according to the present invention, e.g. constructs of the invention containing the apoptotic inducer TRAIL or FasL as segment (1), applies particularly to all those members of the family of TNF ligands which are exclusively or in an especially high degree active as a membrane molecule for certain receptors. Apart from TRAIL, also TNF (analogously to TRAIL relating to TNF-R2) and also, for example, the immunomodulators CD40L and CD30L belong thereto. Therefore, especially preferred are such polypeptides according to the present invention which recognise a cell membrane-bound cytokine receptor as specific target molecule. Thereto belong also in a non-limiting list e.g. following ligands: TNFSF1 (LTalpha), TNFSF2 (TNF), TNFSF3 (LTbeta), TNFSF4 (OX40L), TNFSF5 (CD40L), TNFSF6 (FasL), TNFSF7 (CD27L), TNFSF8 (CD30L), TNFSF9 (4-1BBL), TNFSF10 (TRAIL), TNFSF11 (RANKL), TNFSF12 (TWEAK), TNFSF13 (APRIL), TNFSF13B (BLYS), TNFSF14 (LIGHT), TNFSF15 (VEGI), TNFSF16 (CD30L), TNFSF18 (AITRL) and EDA. These or their fragments or corresponding functional variants of the native sequence or of the fragments can also serve as segment (1) in a construct of the present invention. In this context, in particular all membrane-bound type 2 proteins (extracellular C-terminus), the fragments or functional derivates thereof, which depend on a terminus), the fragments or functional derivates thereof, which depend on a trimeric organisation of their subunits as a prerequisite for their biological activity, are disclosed.

The linker segment (2) between segments (1) and (3) (cytokine and antibody module, respectively) of the polypeptide constructs of the present invention represents, e.g. a flexible linkage, preferably, however, without negatively influencing the trimerisation properties of the corresponding cytokine, as shown in the examplary constructs (C), (D) and (F) (linker amino acid sequence AAAVELE (SEQ ID NO:21), cf. FIG. 4). Linkers having intrinsic di- or multimerisation properties (e.g. tri- or hexamers) are preferably chosen, e.g. in order to achieve an increased stability of the multimeric constructs, e.g. by intrinsic structural properties of the linker peptide such as coiled-coil structures and/or the formation of intermolecular disulfide bridges resulting in covalent linkages. In this case the linker (segment (2)) represents a polymerisation module.

In the case of a linker acting as a trimerisation module (linker type 2a), for example an immunoglobulin hinge region and CH3 domain of a human immunoglobulin gene (AA368-489, human IgG1, NCBI Accession No. AAF21613) is preferred (linker in examplary construct (A), cf. FIG. 4). A trimerisation module (linker type 2b) as the linker can be formed from, for example, a domain of the Tenascin molecule (AA110-139, Swiss Prot. Accession No. P10039, chicken; or Swiss Prot. Accession No. P24821, human). Finally, a linker as a hexamerisation module, thus having hexamerisation properties, can comprise a domain of the Tenascin molecule being extended in comparison to linker type 2b (AA 34-139, Swiss Port. Accession No. P10039, chicken; or Swiss Port. Accession No. P24821, human) (linker type 2c). In any case, the sequences of native polypeptides or fragments of these native polypeptides, which are employed as the linker in segment (2) of the polypeptide according to the present invention, may also be present in form of biologically active variants thereof in the sense of the invention and according to the definition given above.

Alternatively, other naturally occurring or synthetically produced linker peptides are envisaged in segment (2). In principle, a linker may correspond to a native or varied (partial) sequence of all organisms, preferably from vertebrates, in particular from mammals, especially from humans. Further, for example, all sequence segments of proteins are suitable as linkers, which generate di- or multimers by the formation of super secondary structures, e.g. "coiled-coil-helices" or typical triple helices of the collagen type (e.g. CMP, COMP, collagen, laminin). Also, segments of proteins of the C1q-family or of collectines are typically suitable for di- or multimerisation. For example, the extracellular domain of a member of the family of TNF ligands as segment (1) of a polypeptide according to the present invention can be expressed in form of a pentamer by recombination with the corresponding pentamerisation domains of COMP as linker segment (2). According to the present invention, these can be homo- or heterodi- or multimers of fusion proteins of the present invention.

Further preferred in the context of the present invention are such polypeptides wherein the segment (3) thereof contains an antigen binding antibody or an antigen binding antibody fragment. At this, a polypeptide of the present invention will then be especially preferred, when the segment (3) is an antibody or an antibody fragment of a mammal, in particular of murine or human origin, or a humanised antibody or a humanised antibody fragment, for example of mammalian origin. In the case of the humanisation, the segment (3) typically consists of an scFv of murine, humanised by CDR grafting or totally human origin, being produced according to the prior art.

Segment (3) of a polypeptide according to the present invention preferably has a specifity for an antigen being selectively or predominantly expressed in the tumour tissue. In principle, this tumour antigen can be expressed on the malignant cells themselves or also in the non-malignant part of the tumour, the stroma cells or the tumour endothelium. Such antigens of non-malignant tissue parts of a solid tumour (carcinoma) are, on the one hand, genetically invariant, on the other hand, they are present in diverse tumour entities and are, therefore, universal tumour markers. Examples of such tumour antigens, against which an antibody or antibody fragment of fragment (3) of the polypeptide according to the present invention may be directed, are the VEGFR and the VEGFR/VEGF complex, respectively, as well as Integrin $a_v\beta_3$ and the fibronektin isoform $\beta$Fn as largely selective target structures of the tumour endothelium and the fibroblast activation protein (FAP) as a selective marker of the tumour stromas. All above-mentioned examples can be captured with specific scFvs. For this reason, such scFvs ("single chain Fv") are especially suitable as segment (3) in an antibody according to the present invention.

Therefore, preferred for segment (3) of a polypeptide according to the present invention are antibody fragments in various antibody forms, e.g. scFv, Fab or complete immunoglobulin.

Accordingly, a preferred polypeptide according to the present invention (examples see FIGS. 2 and 3) represents a recombinant, homo-di- or -trimeric fusion protein, in principle containing the following structural elements in a defined sequence (monomer): (segment (3)) N-terminally a murine, humanised or human single chain antibody fragment (scFv) consisting of VH-peptide-linker-VL; (segment (2)) a linker sequence with or without covalent multimerisation properties, e.g. a dimerisation (2a), trimerisation (2b) or hexamerisation domain (2c); (segment (1)) C-terminally the human extracellular domain of TRAIL (AA 95-281, NCBI Accession No. U37518) or of FasL (AA 139-281, NCBI Accession No. U11821). Analogously, for example CD40L or other cytokine members of the TNF family may serve as segment (1) of corresponding polypeptides according to the present invention.

In the context of the present invention are also disclosed all di- or multimers resulting from constructs according to the present invention by specific choice of the linker (2), to which the whole disclosure with respect to the constructs according to the present invention identically refers. In so far a di- or multimer of polypeptides according to the present invention in accordance with the present disclosure always falls under the broader expression "polypeptide according to the present invention".

Further subject matter of the present invention are DNA sequences encoding fusion proteins of the above-mentioned type of the present invention (nucleic acid constructs) or which contain such a region encoding a polypeptide according to the present invention. Such DNA sequences are expressed in expression vectors, whereby also the corresponding expression vectors containing a DNA sequence for the fusion proteins according to the present invention belong to the subject matter of the present invention. Preferably, vectors according to the present invention are capable of expression and/or amplification in a prokaryotic and/or eukaryotic cell. In particular, the present invention relates to plasmid vectors, e.g. pBABEpuro, or also retroviral vectors, in particular also all such vector systems that can be applied in gene therapy, e.g. also adenoviral vector systems. Therefore, in the context of the present invention, there are also disclosed gene therapeutic methods using vectors according to the present invention or nucleic acids constructs as a method of treatment for the medical indications which are disclosed according to the present invention.

Furthermore, the present invention pertains to such host cells which are transfected with DNA sequences (nucleic acid constructs) encoding fusion proteins according to the present invention. In this context, especially preferred are host cells being transfected with expression vectors or nucleic acid constricts according to the present invention, wherein the expression vectors again contain DNA sequences coding for the fusion proteins according to the present invention. The nucleic acid constructs are characterized in that they contains a nucleotide sequence coding for a polypeptide according to any one of the preceeding claims.

Further subject matter of the present invention are methods for the production (expression and isolation) of polypeptides according to the present invention, wherein an isolation method according to the present invention is typically characterised by (a) providing a vector or nucleic acid construct according to the present invention, (b) transfecting cells with a vector or nucleic acid construct obtained according to method step (a), (c) culturing the cells transfected according to (b), and (d) isolating polypeptides of the present invention, being expressed under appropriate conditions, from the host cells and/or the culture supernatant. The expression of the fusion protein is typically carried out in suitable expression systems according to the prior art, preferably as a secreted product of stable transfectants, e.g. CHO cells, or in other animal cells such as Cos7 or Sf9 (insect cells) or other eukaryotic cell systems, e.g. *Pichia pastoris*. Preferably, the expressed polypeptides according to the present invention will contain respective leader sequences suitable for the secretion in the cell system. Therefore, the vectors according to the present invention used for expression will also contain coding regions encoding a functional leader sequence, e.g. as described in Brocks et al. (Immunotechnology 3: 173-184, 1997) for mammalian and insect cells, or pPICZalpha-vectors (INVITROGEN) for expression and secretion in the yeast *Pichia pastoris*.

Polypeptides according to the present invention, but optionally also nucleic acid constructs, vectors or host cells (summarized here under the category "substances according to the present invention") are also considered as medicaments or for the preparation of a medicament. They are especially of use in case substances according to the present invention are to exert their full biological activity via the corresponding cytokine receptor after antibody-mediated binding of the fusion protein to a specific target molecule expressed on the cell membrane. By suitably choosing the antibody specificity, the cytokine activity of the substance according to the present invention is directed to the tissue to be treated, e.g. a tumour tissue, and a therapeutic agent can be produced which is specifically designed/optimised for the respective indication/tumour entity. For example, in the application as a tumour therapeutic agent, in particular for the treatment of solid tumours but also of lymphatic tumours (benign or malignant), at first a polypeptide according to the present invention is specifically enriched after application in vivo due to the antibody moiety in the tumour area by membrane markers formed by the tumour itself or by the reactive tumour stroma/tumour vascular system and there it is presented to cytokine receptor-positive tumour cells or cytokine sensitive cells of the reactive tumour supplying normal tissue.

The use of substances according to the present invention is in principle also always then desirable for the application in therapy when the activation of a signal transduction pathway, e.g. the signal cascades triggered by the TNF receptor family, e.g. an apoptotic signal cascade, is to be triggered. Therefore, the use of substances according to the present invention for the treatment or for the production of a medicament for the treatment of all hyperproliferative disorders is disclosed, e.g. also for the targeted elimination of cells of the immune system in case of excessive immune reactions, e.g. autoimmune diseases such as multiple scleroses, rheumatoid arthritis, diabetes mellitus and TEN, or misguided immune reactions against foreign antigens occurring in case of, e.g. infectious diseases (bacterial (for example by myco-bacteria), viral or protozoological). Further is disclosed the treatment of metabolic diseases or general hyperinflammatory conditions, in particular chronic inflammations, e.g. also allergies, but also the treatment of rejection reactions of the immune system of a patient against foreign tissues. In the cases mentioned above, the respective antigen binding segment (3) of a polypeptide according to the present invention must recognize characteristic markers of the surface of the target cells in which preferably an apoptotic signal cascade with the object of cell death is to be triggered. Therefore, in the case of the treatment after transplantation of foreign tissue, e.g. the endogenic cells of the immune system of the transplantation patient responsible for the rejection reaction will serve as the target cells.

The subject matter of the present invention such as nucleic acid constructs, expression vectors or host cells are—as disclosed above—also described as medicaments, e.g. for the treatment of the diseases mentioned above. In this case, preferably cells to be transfected are taken from the patient to be treated, said cells are transfected in vitro with expression vectors according to the present invention, cultured and then transferred into the patient as a retransplant. The transfection is preferably carried out by nucleic acid constructs or expression vectors which combine the expression with a controllable promoter. The transfected endotransplant may be, for example, locally injected—depending on the specific disease and the specific target cells. A local administration is, e.g. in the case of a tumour therapy, preferred. At this, tumour cells are taken from the patient, transfected in vitro and then, if possible, injected directly into the tumour, e.g. in the treatment of dermal tumours (e.g. melanomas), tumours of the nerve system (e.g. glioblastomas).

Further subject matter of the present invention is a composition containing polypeptides, nucleic acid constructs, vectors and/or host cells according to the present invention as well as pharmaceutically acceptable excipients, additives and/or carriers (e.g. also solubilisers). Therefore, the present invention discloses a combination of substances according to the present invention with pharmaceutically acceptable carriers, excipients and/or additives. Corresponding ways of production are disclosed in "Remington's Pharmaceutical Sciences" (Mack Pub. Co., Easton, Pa., 1980) which is part of the disclosure of the present invention. As carrriers for parenteral administration are disclosed, e.g., sterile water, sterile sodium chloride solutions, polyalkylene glycols, hydrogenated naphthalenes and, in particular biocompatible lactid polymers, lactid/glycolid copolymer or polyoxyethylene/polyoxypropylene copolymers. Such compositions according to the present invention are envisaged for all medical indications as disclosed above. Moreover, compositions according to the present invention may contain fillers or substances such as lactose, mannitol, substances for covalently linking of polymers such as, for example, polyethylene glycol to inhibitors of the present invention, for complexing with metal ions or for inclusion of materials into or on special preparations of polymer compounds such as, for example, polylactate, polyglycolic acid, hydrogel or onto liposomes, microemulsions, micells, unilamellar or multilamellar vesicles, erythrocyte fragments or spheroplasts. The particular embodiments of the compositions are chosen depending on the physical behaviour, for example with respect to the solubility, stability, bioavailability or degradability. A controlled or constant release of the active substance of the present invention in the composition includes formulations on the basis of lipophilic depots (e.g. fatty acids, waxes or oils). In the context of the present invention are also disclosed coatings of substances or compositions according to the present invention containing such substances, that is to say coatings with polymers (e.g. polyoxamers or polyoxamines). Furthermore, substances or compositions according to the present invention may comprise protective coatings such as protease inhibitors or permeability amplifying agents.

In principle, in the context of the present invention, all administration pathways known in the prior art for substances or compositions according to the present invention are disclosed. Preferably, the preparation of a medicament for the treatment of the diseases or disorders mentioned above is carried out via the parenteral, i.e., for example, subcutaneous, intramuscular or intravenous, oral or intranasal administration pathway. Typically, pharmaceutical compositions according to the present invention will be solid, liquid or in the form of an aerosol (e.g. spray)—depending on the type of formulation.

In summary, according to the present invention it can be noted that antibody-cytokine fusion proteins having proapoptotic and immunomodulating properties are provided containing soluble forms of a priori membrane-bound cytokines. By way of the antibody function being present in the polypeptide according to the present invention, by binding to a specific cell membrane-bound target molecule the cytokines, which otherwise have no or a limited activity, exert their full biological cytokine activity via the corresponding cytokine receptor(s). By suitably choosing the antibody specificity, the cytokine activity is directed to the tissue, e.g. tumour tissue, to be treated, and a therapeutic agent can be prepared which is specifically designed/optimised for the respective indication/tumour entity. In all, the selectivity of the cytokine activity in the polypeptides according to the present invention is achieved by two mechanisms: On the one hand via the antibody-mediated, e.g. scFv, selective enrichment of the cytokine in the tumour, the cytokine which has no or a limited activity in the non-antigen-bound state, and on the other hand through the site-specific activation of the cytokine via presentation into a molecule being fully capable of signalling, in particular also an apoptosis inducing molecule.

The present invention is further illustrated by the following figures.

FIG. 1 shows the result of a gelelectrophoretic separation after expression of a fusion protein according to the present invention (structure of the fusion protein see Example 1, TRAIL-AMAIZe(MBOS4), abbreviated in FIG. 1 as MBOS4-TRAIL). The Western blot analysis shows that the fusion protein results in a band of approximately 140 kDa under non-reducing conditions, which corresponds well with the calculated MW of the CH3-linked dimer of 2×65=130 kDa.

Figure 2:
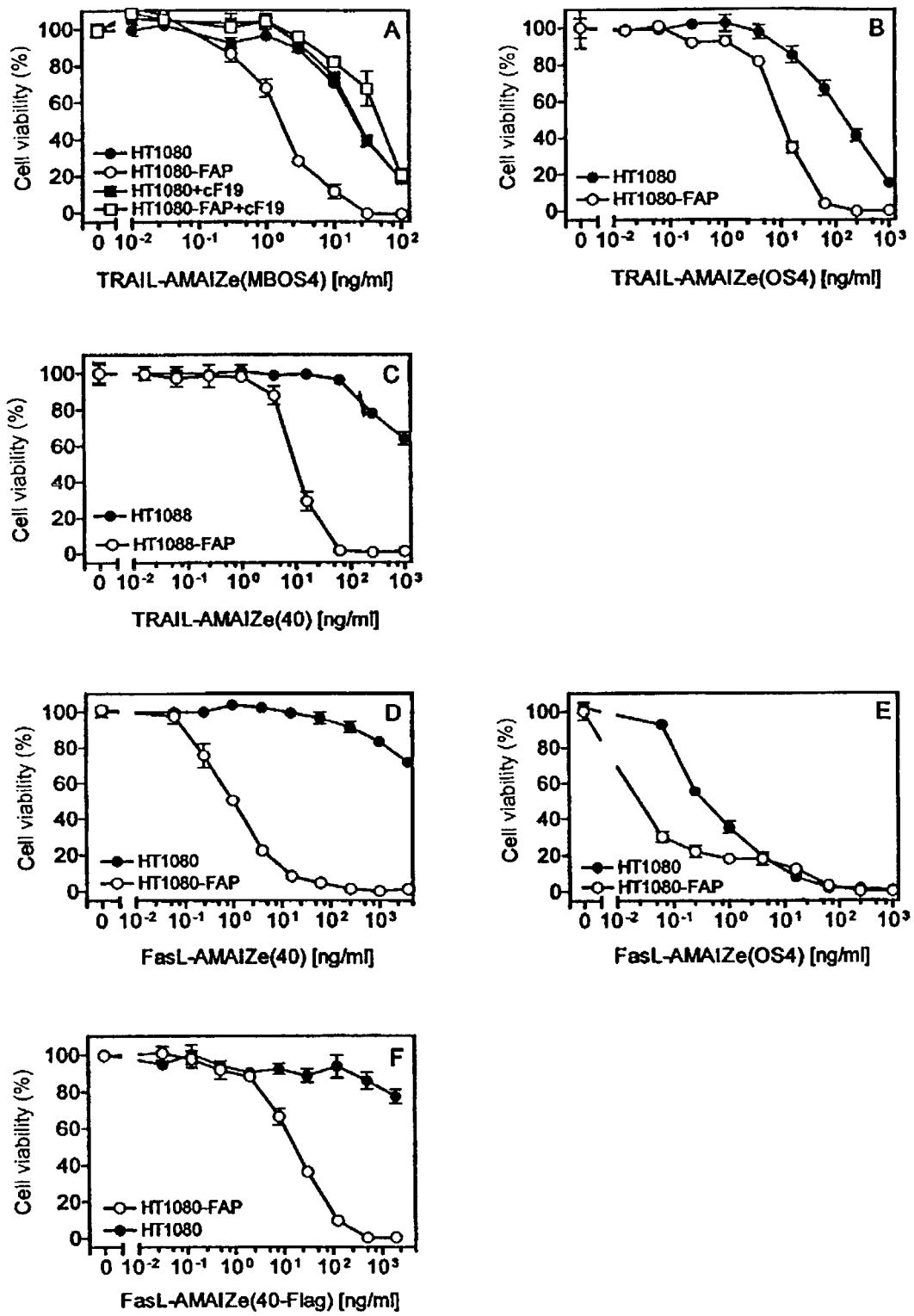

FIG. 2 depicts the results of studies with respect to a preferential induction of apoptosis of FAP-positive tumour cells by several AMAIZe-polypeptide examples according to the present invention. FIG. 2 shows in all panels (FIG. 2A to 2F) a plot of the cell activity (in %) against the concentration of the respective indicated AMAIZe proteins. The curves drawn in FIG. 2A (legend in FIG. 2) represent the results of the treatment of FAP-positive (HT1080-FAP) or FAP-negative (HT 1080) cells with TRAIL-AMAIZe(MBOS4) after preincubation with the FAP-specific antibody cF19 or without a corresponding preincubation.

In all further illustrated cases (FIG. 2B-F), it can be recognized that the cytotoxicity of the different AMAIZe constructs is always larger on the antigen-expressing cells (HT1080-FAP), i.e. those cells to which the AMAIZe constructs according to the present invention bind by antibody mediation, than with respect to the corresponding antigen-negative parental cells (HT1080).

The dependency of the increased sensitivity of FAP-expressing cells on the binding of the AMAIZe constructs to FAP is shown as an example in FIG. 2A: here, by competition of a Fap-specific antibody cF19 (cF19, black squares) with the AMAIZe construct TRAIL-AMAIZe(MBOS4) for the binding to the cellularly expressed FAP, the cytotoxic activity of this AMAIZe-construct with respect to the FAP-positive cell is reduced to a degree as it is also observed in the case of Fap-negative cells. In contrast thereto, the addition of cF19 has no influence on FAP-negative cells. Thus, the antibody-mediated specifity is unambigously demonstrated by competitive inhibition of the amplified induction of apoptosis via the FAP-specific monoclonal antibody cF19.

FIG. 3 shows examples of AMAIZe constructs of the present invention with TRAIL and with FasL as the cytokine module, the independent FAP-specific antibodies clone OS4 and clone 40 as well as different linkers between the antibody and the cytokine module (constructs (A)-(F)) according to the present invention). All constructs according to the present invention have the property of an antigen-dependent induction/amplification of apoptosis.

In the following, the produced constructs are represented schematically. Their specific AMAIZe activity (preferential induction of apoptosis in antigen-positive cells) is described in FIG. 2. The code chosen for amino acid sequences is the one letter code. Fragment (2) (linker) forms the linkage between segment (3) (e.g. scFv) and the cytokine moiety (1) (e.g. TRAIL or FasL in the constructs shown) in the molecule according to the present invention and, in the case of the use of special linkers such as that of the type 2a, 2b or 2c, ensures at the same time the covalent linkage of the human protein during biogenesis.

Construct (A): TRAIL-AMAIZe(MBOS4)

NH$_2$-[Leader]-[OS4-VH/VL]-[Linker1]-[CH3]-[Linker2]-[TRAIL(95-281)]-COOH

| | |
|---|---|
| OS4-VH/VL: | FAP-specific human single chain antibody fragment |
| CH3: | CH3 domain (AA 363-489) of a human IgG1 |
| Linker 1: | hinge region of a human IgG1 (bold) with a C-terminal poly-Gly linker (italic) (RTVAAPSVFAVFAAAVEPKSCDKTHTCPPC_GGGSSGGGSG_; SEQ ID NO: 18) |
| Linker 2: | poly-Gly linker (GGGGTGGGS; SEQ ID NO: 19) |
| TRAIL (95-281): | extracellular domain of human TRAIL (AA 95-281) |

The linker of construct (A): TRAIL-AMAIZe(MBOS4) has dimerisation properties.

Construct (B): TRAIL-AMAIZe(OS4)

NH$_2$-[Leader]-[OS4-VH/VL]-[Linker]-[TRAIL(95-281)]-COOH

| | |
|---|---|
| OS4-VH/VL: | FAP-specific human single chain antibody fragment |
| Linker: | RTVAAPSVFAVFAAAVELE (SEQ ID NO: 20) |
| TRAIL (95-281): | extracellular domain of human TRAIL (AA 95-281) |

Construct (C): TRAIL-AMAIZe(40)

NH$_2$-[Leader]-[40-VH/VL]-[Linker]-[TRAIL(95-281)]-COOH

| | |
|---|---|
| 40-VH/VL: | FAP-specific human single chain antibody fragment |
| Linker: | AAAVELE (SEQ ID NO: 21) |
| TRAIL (95-281): | extracellular domain of human TRAIL (AA 95-281) |

Construct (D): FasL-AMAIZe(40)

NH$_2$-[Leader]-[40-VH/VL]-[Linker]-[FasL(139-281)]-COOH

| | |
|---|---|
| 40-VH/VL: | FAP-specific human single chain antibody fragment |
| Linker: | AAAVELE (SEQ ID NO: 21) |
| FasL (139-281): | extracellular domain of human FasL (AA 139-281) |

Construct (E): FasL-AMAIZe(OS4)

NH$_2$-[Leader]-[OS4-VH/VL]-[Linker]-[FasL(139-281)]-COOH

| | |
|---|---|
| OS4-VH/VL: | FAP-specific human single chain antibody fragment |
| Linker: | RTVAAPSVFAVFAAA (SEQ ID NO: 22) |
| FasL (139-281): | extracellular domain of human FasL (AA 139-281) |

Construct (F): FasL-AMAIZe(40-Flag)

NH$_2$-[Leader]-[40-VH/VL]-[Flag-tag]-[Linker]-[FasL(139-281)]-COOH

| | |
|---|---|
| 40-VH/VL: | FAP-specific human single chain antibody fragment |
| Flag-tag: | DYKDDDDK (SEQ ID NO: 23) |
| Linker: | AAAVELE (SEQ ID NO: 21) |
| FasL (139-281): | extracellular domain of human FasL (AA 139-281) |

The present invention is further illustrated by the following examples.

EXAMPLE 1

Expression of a Fusion Protein According to the Present Invention

A fusion protein according to the invention was expressed in CHO-DG44 cells. This fusion protein is the construct TRAIL-AMAIZe(MBOS4), abbreviated as MBOS4-TRAIL in FIG. 1, (covalent dimer) having the following structure (cf. also FIG. 3): NH$_2$-[Leader]-[OS4-VH/VL]-[Linker1]-[CH3]-[Linker2]-[TRAIL(95-281)]-COOH

| | |
|---|---|
| OS4-VH/VL: | FAP-specific human single chain antibody fragment |
| CH3: | CH3 domain (AA 363-489) of a human IgG1 |
| Linker1: | hinge region of a human IgG1 (bold) with a C-terminal poly-Gly linker (italic) (RTVAAPSVFAVFAAAVEPKSCDKTHTCPPC_GGGSSGGGSG_; SEQ ID NO: 18) |
| Linker2: | poly-Gly linker (GGGGTGGGS; SEQ ID NO: 19) |
| TRAIL (95-281): | extracellular domain of human TRAIL (AA 95-281) |

EXAMPLE 2

Construction of the Polypeptides FasL-AMAIZe(40) and TRAIL-AMAIZe(40) According to the Invention The fusion proteins were produced as follows:

1. The single chain antibody fragment (scFv) No. 40 (in the following designated as 40) was isolated according to standard methods based on the binding to FAP from a scFv phage expression library which was present in the vector pSEX (see Brocks et al., Molecular Medicine 7: 461-469; Mersmann et al., Int. J. Cancer 92: 240-248).

2. The scFv 40 was excised from pSEX with Pvu2 and Not1 and was inserted into the corresponding sites of the minibody construct pW6 (Wüest, T., Dissertation, University of Stuttgart, 2001). For this purpose, the DNA region located between these sites was removed from the plasmid pW6 by a corresponding restriction digest and preparative agarose gelelectrophoresis together with DNA elution. By this cloning step, scFv 40 was cloned between an eukaryotic Ig leader sequence (upstream of 40) and the constant region (Fc region) of a human antibody (IgG1, downstream of 40) such that the expression of a divalent minibody, as described by Hu et al. (Cancer Research 56: 3055), is possible.

3. Leader+scFv 40+Fc were amplified by proof-reading PCR using primers 1 and 2, and the scFv fragment was inserted into the corresponding restriction sites of the eukaryotic expression vector pcDNA3.1 (Invitrogen) by means of the Kpn1 restriction the site introduced by primer 1 and the Not1 restriction site located between scFv 40 and the Fc-region.

4a. For the final preparation of FasL-AMAIZe(40), AA 139 to 281+stop codon of human FasL were amplified by means of proof-reading PCR using primers 3 and 4 and inserted into the Not1 and Xba1 restrictions sites of the pcDNA3.1 cloning intermediate obtained in 3. For this purpose, a Not1 and a Nhe1, compatible with Xba1, restriction site were introduced into the FasL amplicon by the primers used. The thus obtained final construct allows the expression of the fusion protein FasL-AMAIZe(40).

4b. For the final preparation of TRAIL-AMAIZe(40), AA 95 to 281+stop codon of human TRAIL were amplified by proof-reading PCR using primers 5 and 6 and inserted into the restrictions sites Not1 and Xba1 of the pcDNA3.1 cloning intermediate obtained in 3. For this purpose, a Not1 and a Xba1 restriction site were introduced into the TRAIL amplicon by the primers used. The thus obtained final construct allows the expression of the fusion protein TRAIL-AMAIZe(40).

5. For recovering TRAIL-AMAIZe(40) and FasL-AMAIZe (40), respectively, HEK293 cells were transfected with a construct described in 4. using lipofectamine (Gibco-BRL) according to the manufactures instructions. 48 hours after transfection, the AMAIZe construct supernatants were sterile filtered and stored at 4° C. until further used.

All cloning and PCR amplification steps were carried out according to customary standard procedures using the following primers. All constructs were sequenced for the verification of the CDNA sequence.

```
Primer 1
                                                       (SEQ ID NO: 24)
5'CGG GGT ACC TCG ACC ATG GAG TGG ACC TGG CGC GTG 3'

Primer 2
                                                       (SEQ ID NO: 25)
5'CCG GAA TTC CAC AGC CAG GTG CAA CTA GTT GAG CC 3'

Primer 3
                                                       (SEQ ID NO: 26)
5'CTA GGT GCG GCC GCA GTT GAG CTC GAG GAA AAA AAG GAG CTG AGG AAA GTG 3'

Primer 4
                                                       (SEQ ID NO: 27)
5'CTA GCT AGC GTG CTT CTC TTA GAG CTT ATA TAA GCC 3'

Primer 5
                                                       (SEQ ID NO: 28)
5'GTC TTC GCG GCC GCA GTT GAG CTC-
  GAG ACC TCT GAG GAA ACC ATT TCT ACA G 3'

Primer 6
                                                       (SEQ ID NO: 29)
5'TGC TCT AGA CCA GGT CAG TTA GCC AAC TAA AAA GGC 3'
```

EXAMPLE 3

Demonstration of the Antigen-Dependent Activation by FAP-Specific TRAIL-AMAIZe(MBOS4) as an Example (See Also FIG. 2A)

TRAIL-AMAIZe(MBOS4) was provided in analogy to the description in Example 2.

Subsequently, FAP-positive (HT1080-FAP) and FAP-negative (HT1080) cells were either preincubated (1 h) with the FAP-specific antibody cF19 or remained untreated. The cells were incubated over night in the presence of CHX (2.5 µg/ml) with the indicated concentrations of TRAIL-AMAIZe (MBOS4). The quantification of the surviving cells was carried out by means of crystal violet staining. FIG. 2A depicts the activity of TRAIL-AMAIZe(MBOS4) on target cells which are specifically recognized by the antibody moiety of the fusion protein (FAP-positive HT 1080).

EXAMPLE 4

Preferential Induction of Apoptosis by TRAIL-AMAIZe and FasL-AMAIZe in FAP-Positive Tumour Cells (See Also FIG. 2A-F)

$15 \times 10^3$ HT1080 or HT1080-FAP cells per well of a 96-well plate were cultured over night. On the next day, the cells were treated with the indicated amounts of the different constructs for further 14 to 18 hours in the presence of 2.5 µg/ml CHX (for the sensitisation of the cells with respect to the induction of the death receptor-mediated apoptosis). Finally, the viability of the cells was determined by staining with crystal violet. The respective values for untreated groups were in all cases between 700 and 850 mOD. Control groups in which all cells were prone to cell death showed values of 100 to 150 mOD. The cell death of the corresponding positive control groups was accomplished by secondary cross-linking of a soluble Flag-labelled FasL construct (500 ng/ml) by means of the Flag-specific antibody M2 (Sigma). Also in this case 2.5 µg CHX were added to the cultures.

All publications, patents, and patent applications are incorporated by reference herein, as though individually incorporated by reference.

What is claimed is:

1. A polypeptide comprising:
   (i) a segment (1) that is FasL extracellular domain consisting of the amino acid sequence of SEQ ID NO: 14;
   (ii) a segment (2) comprising a non-multimerizing peptide linker that is linked to the N-terminus of segment (1), wherein the amino acid sequence of the linker consists of the sequence selected from the group consisting of AAAVELE (SEQ ID NO: 21), RTVAAPSVFAV-FAAAVELE (SEQ ID NO: 20) and RTVAAPSVFAV-FAAA (SEQ ID NO: 22); and
   (iii) a segment (3) comprising a single chain antibody that selectively recognizes a specific fibroblast activation protein (FAP) target molecule on a cell surface, said segment (3) being linked to the N-terminus of segment (2),
wherein the FasL extracellular domain causes formation of a trimer, wherein a trimer of the FasL extracellular domain alone has no or limited biological activity, wherein the biological activity of the FasL extracellular domain trimer is activated upon binding of the segment (3) portion of the polypeptide to the target FAP molecule on the cell surface, and wherein the biological activity comprises the ability to induce apoptosis.

2. A composition comprising a polypeptide according to claim 1, and a pharmaceutically acceptable excipient, additive and/or carrier.

3. A polypeptide comprising:
   (i) a segment (1) consisting of the FasL extracellular domain;
   (ii) a segment (2) comprising a non-multimerizing peptide linker that is linked to the N-terminus of segment (1), wherein the amino acid sequence of the linker consists of the sequence selected from the group consisting of AAAVELE (SEQ ID NO: 21), RTVAAPSVFAV-FAAAVELE (SEQ ID NO: 20) and RTVAAPSVFAV-FAAA (SEQ ID NO: 22); and
   (iii) a segment (3) comprising a single chain antibody that selectively recognizes a target molecule on a cell surface, said segment (3) being linked to the N-terminus of segment (2),
wherein the FasL extracellular domain causes formation of a trimer, wherein a trimer of the FasL extracellular domain alone has no or limited biological activity, wherein the biological activity of the FasL extracellular domain trimer is activated upon binding of the segment (3) portion of the polypeptide to the target molecule on the cell surface, and wherein the biological activity comprises the ability to induce apoptosis.

* * * * *

UNITED STATES PATENT AND TRADEMARK OFFICE
CERTIFICATE OF CORRECTION

PATENT NO. : 8,980,265 B2
APPLICATION NO. : 10/389223
DATED : March 17, 2015
INVENTOR(S) : Pfizenmaier et al.

It is certified that error appears in the above-identified patent and that said Letters Patent is hereby corrected as shown below:

On the title page, item (54), in "Title", and in the specification, in column 1, line 3, delete "AMAIZEE" and insert --AMAIZe--, therefor.

Signed and Sealed this
Eighteenth Day of August, 2015

Michelle K. Lee
*Director of the United States Patent and Trademark Office*